United States Patent
Iaccino et al.

(10) Patent No.: US 7,795,490 B2
(45) Date of Patent: Sep. 14, 2010

(54) PRODUCTION OF AROMATICS FROM METHANE

(75) Inventors: Larry L. Iaccino, Seabrook, TX (US); Elizabeth L. Stavens, Seabrook, TX (US); Neeraj Sangar, League City, TX (US); Jeremy J. Patt, League City, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 812 days.

(21) Appl. No.: 11/787,958

(22) Filed: Apr. 18, 2007

(65) Prior Publication Data

US 2007/0249880 A1  Oct. 25, 2007

Related U.S. Application Data

(60) Provisional application No. 60/794,280, filed on Apr. 21, 2006, provisional application No. 60/794,058, filed on Apr. 21, 2006.

(51) Int. Cl.
*C07C 2/78* (2006.01)

(52) U.S. Cl. ................ 585/943; 585/324; 585/357; 585/355; 585/407; 585/379; 585/540

(58) Field of Classification Search ........... None
See application file for complete search history.

(56) References Cited

U.S. PATENT DOCUMENTS

| | | | |
|---|---|---|---|
| 4,727,206 A | 2/1988 | Clayson et al. | |
| 5,026,937 A | 6/1991 | Bricker | |
| 5,336,825 A | 8/1994 | Choudhary et al. | |
| 5,866,737 A * | 2/1999 | Hagemeyer et al. | 585/443 |
| 6,239,057 B1 | 5/2001 | Ichikawa et al. | |
| 6,426,442 B1 | 7/2002 | Ichikawa et al. | |
| 2003/0083535 A1 | 5/2003 | Wright et al. | |
| 2004/0015025 A1 * | 1/2004 | Bellussi et al. | 585/319 |

FOREIGN PATENT DOCUMENTS

| | | |
|---|---|---|
| WO | 03/000826 | 1/2003 |
| WO | 2006/083409 | 8/2006 |

OTHER PUBLICATIONS

Japan Chemical Week Incorporating Asia Report, "Benzene Synthesized Directly from Methane: Mitsubishi Chem", The Chemical Daily Co., Ltd., vol. 46, No. 2337, ISSN 0047-1755, Oct. 6, 2005.

* cited by examiner

*Primary Examiner*—Tam M Nguyen
(74) *Attorney, Agent, or Firm*—Andrew B. Griffis

(57) ABSTRACT

In a process for converting methane to aromatic hydrocarbons, a feed containing methane is supplied to one or more reaction zone(s) containing catalytic material operating under reaction conditions effective to convert at least a portion of the methane to aromatic hydrocarbons; the reaction zone(s) being operated with an inverse temperature profile.

23 Claims, 2 Drawing Sheets

PRODUCTION OF AROMATICS FROM METHANE

CROSS REFERENCE TO RELATED APPLICATIONS

This application claims the benefit of Provisional Application No. 60/794,280 filed Apr. 21, 2006, the disclosures of which are incorporated by reference in their entireties. This application also claims the benefit of Provisional Application No. 60/794,058 filed Apr. 21, 2006, the disclosures of which are incorporated by reference in their entireties.

FIELD

This invention relates to a process for producing aromatic hydrocarbons from methane and, in particular, from natural gas.

BACKGROUND

Aromatic hydrocarbons, particularly benzene, toluene, ethylbenzene and xylenes, are important commodity chemicals in the petrochemical industry. Currently, aromatics are most frequently produced from petroleum-based feedstocks by a variety of processes, including catalytic reforming and catalytic cracking. However, as the world supplies of petroleum feedstocks decrease, there is a growing need to find alternative sources of aromatic hydrocarbons.

One possible alternative source of aromatic hydrocarbons is methane, which is the major constituent of natural gas and biogas. World reserves of natural gas are constantly being upgraded and more natural gas is currently being discovered than oil. Because of the problems associated with transportation of large volumes of natural gas, most of the natural gas produced along with oil, particularly at remote places, is flared and wasted. Hence the conversion of alkanes contained in natural gas directly to higher hydrocarbons, such as aromatics, is an attractive method of upgrading natural gas, providing the attendant technical difficulties can be overcome.

A large majority of the processes currently proposed for converting methane to liquid hydrocarbons involve initial conversion of the methane to synthesis gas, a blend of $H_2$ and CO. However, production of synthesis gas is capital and energy intensive and hence routes that do not require synthesis gas generation are preferred.

A number of alternative processes have been proposed for directly converting methane to higher hydrocarbons. One such process involves catalytic oxidative coupling of methane to olefins followed by the catalytic conversion of the olefins to liquid hydrocarbons, including aromatic hydrocarbons. For example, U.S. Pat. No. 5,336,825 discloses a two-step process for the oxidative conversion of methane to gasoline range hydrocarbons comprising aromatic hydrocarbons. In the first step, methane is converted to ethylene and minor amounts of $C_3$ and $C_4$ olefins in the presence of free oxygen using a rare earth metal promoted alkaline earth metal oxide catalyst at a temperature between 500° C. and 1000° C. The ethylene and higher olefins formed in the first step are then converted to gasoline range liquid hydrocarbons over an acidic solid catalyst containing a high silica pentasil zeolite.

However, oxidative coupling methods suffer from the problems that they involve highly exothermic and potentially hazardous methane combustion reactions and they generate large quantities of environmentally sensitive carbon oxides.

A potentially attractive route for upgrading methane directly into higher hydrocarbons, particularly ethylene, benzene and naphthalene, is dehydroaromatization or reductive coupling. This process typically involves contacting the methane with a catalyst comprising a metal, such as rhenium, tungsten or molybdenum, supported on a zeolite, such as ZSM-5, at high temperature, such as 600° C. to 1000° C. Frequently, the catalytically active species of the metal is the zero valent elemental form or a carbide or oxycarbide.

For example, U.S. Pat. No. 4,727,206 discloses a process for producing liquids rich in aromatic hydrocarbons by contacting methane at a temperature between 600° C. and 800° C. in the absence of oxygen with a catalyst composition comprising an aluminosilicate having a silica to alumina molar ratio of at least 5:1, the aluminosilicate being loaded with (i) gallium or a compound thereof and (ii) a metal or a compound thereof from Group VIIB of the Periodic Table.

In addition, U.S. Pat. No. 5,026,937 discloses a process for the aromatization of methane which comprises the steps of passing a feed stream, which comprises over 0.5 mole % hydrogen and 50 mole % methane, into a reaction zone having at least one bed of solid catalyst comprising ZSM-5, gallium and phosphorus-containing alumina at conversion conditions which include a temperature of 550° C. to 750° C., a pressure less than 10 atmospheres absolute (1000 kPa) and a gas hourly space velocity of 400 to 7,500 $hr^{-1}$.

Moreover, U.S. Pat. Nos. 6,239,057 and 6,426,442 disclose a process for producing higher carbon number hydrocarbons, e.g., benzene, from low carbon number hydrocarbons, such as methane, by contacting the latter with a catalyst comprising a porous support, such as ZSM-5, which has dispersed thereon rhenium and a promoter metal such as iron, cobalt, vanadium, manganese, molybdenum, tungsten or a mixture thereof. After impregnation of the support with the rhenium and promoter metal, the catalyst is activated by treatment with hydrogen and/or methane at a temperature of about 100° C. to about 800° C. for a time of about 0.5 hr. to about 100 hr. The addition of CO or $CO_2$ to the methane feed is the to increase the yield of benzene and the stability of the catalyst.

Accordingly, there is a need to develop a process for converting methane to higher hydrocarbon(s), which provides high efficiency for heat transfer, adequate hydrocarbon/catalyst contacting, and/or improved process conditions to maximize selectivity to desired higher hydrocarbons, e.g., aromatic compound(s), while minimizing coke formation.

The invention described herein seeks to provide an improved methane aromatization process in which performance is improved by controlling the temperature and composition profile in the reactor system.

SUMMARY

In one aspect, the present invention resides in a process for converting methane to higher hydrocarbons including aromatic hydrocarbons, the process comprising:
  a. providing to the reaction zone a hydrocarbon feedstock containing methane;
  b. providing a quantity of catalytic material within the reaction zone;
  c. maintaining the reaction zone with an inverse temperature profile; and
  d. operating the reaction zone under reaction conditions sufficient to convert at least a portion of the methane to a first effluent having the higher hydrocarbon(s).

In a further aspect, the present invention resides in a process for converting methane to higher hydrocarbons including aromatic hydrocarbons in two or more reaction zones operated in series, the process comprising:

a. providing a quantity of catalytic material within each reaction zone;
b. providing to a first reaction zone a hydrocarbon feedstock containing methane;
c. transfer at least a portion of the effluent of the first reaction zone to a second reaction zone;
d. maintaining the first the reaction zone at a lower average temperature than the second reaction zone; and
e. operating the reaction zones under reaction conditions sufficient to convert at least a portion of the methane to a first effluent having the higher hydrocarbon(s).

DETAILED DESCRIPTION OF THE EMBODIMENTS

Figure 1:
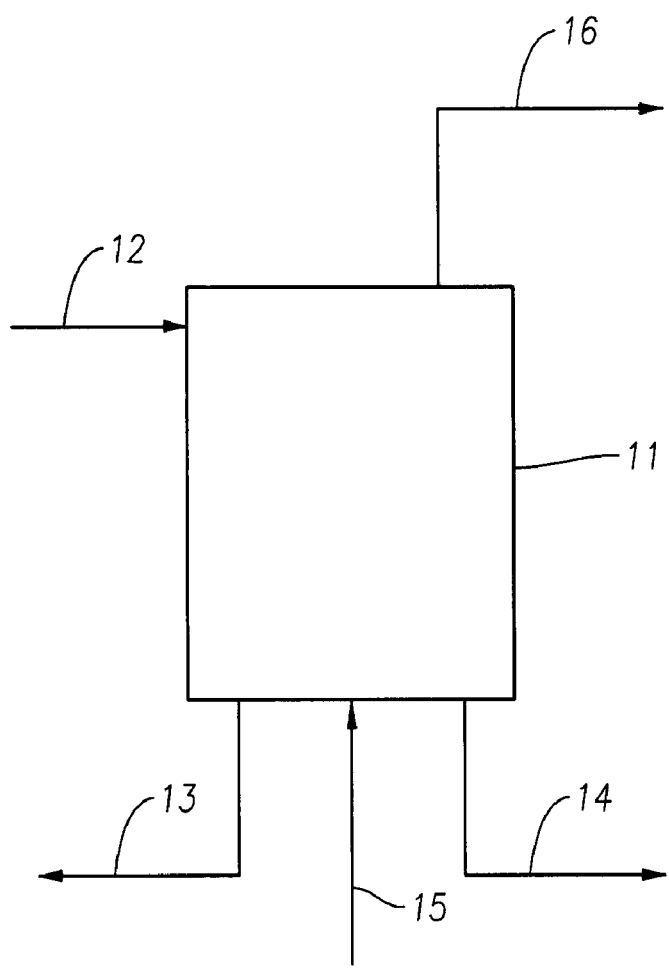
FIG. 1 is a diagram of a process for converting methane to higher hydrocarbons according to a first embodiment of the invention.

As used herein the term "higher hydrocarbon(s)" means hydrocarbon(s) having more than one carbon atom per molecule, oxygenate having at least one carbon atom per molecule, e.g., ethane, ethylene, propane, propylene, benzene, toluene, xylenes, naphthalene, and/or methyl naphthalene; and/or organic compound(s) comprising at least one carbon atom and at least one non-hydrogen atom, e.g., methanol, ethanol, methylamine, and/or ethylamine.

As used herein the term "aromatic hydrocarbon(s)" means molecules containing one or more aromatic rings. Examples of aromatic hydrocarbons are benzene, toluene, xylenes, naphthalene, and methylnaphthalenes.

The terms "coke" and "carbonaceous material" are used herein interchangeably to mean carbon containing materials, which are essentially non-volatile solids at the reaction conditions, with a low hydrogen content relative to carbon content (such as a H/C molar ration of less than 0.8; most probably less than 0.5). These may include crystalline graphite, graphitic sheets, graphitic fragments, amorphous carbon, or other carbon containing structures which are essentially non-volatile solids at the reaction conditions. When reference is made to hard coke, harder coke, or refractory coke; this is meant to be the types of coke either due to structure or location that are harder to remove with the reactant (typically oxygen or hydrogen) being utilized to convert the coke to a gaseous species.

As used herein the term "deactivation" of a catalyst means the loss of catalytic activity and/or selectivity over time. A catalyst is deactivated if its catalytic activity is at least 1% lower, alternatively, at least 5% lower, alternatively, at least 10% lower, alternatively, at least 15% lower, alternatively, at least 20% lower, alternatively, at least 25% lower, alternatively, at least 30% lower, alternatively, at least 35% lower, alternatively, at least 40% lower, alternatively, at least 45% lower, alternatively, at least 50% lower, alternatively, at least 55% lower, alternatively, at least 60% lower, alternatively, at least 65% lower, alternatively, at least 70% lower, alternatively, at least 75% lower, alternatively, at least 80% lower, alternatively, at least 85% lower, alternatively, at least 90% lower, alternatively, at least 95% lower, or alternatively, at least 100% lower, than the catalyst activity of the fresh catalyst or the regenerated catalyst. Not intended to be limited by any theory, we believe that catalyst deactivation may be a phenomenon in which the structure and/or state of the catalyst change, leading to the loss of active sites on the catalyst's surface and thus causing a decrease in the catalyst's performance. For example, catalyst deactivation may be due to coke formation, active site blockage, or dealumination of an aluminosilicate molecular sieve due to steaming.

As used herein the term "moving bed" reactor means a zone or vessel with contacting of solids and gas flows such that the superficial gas velocity (U) is below the velocity required for dilute-phase pneumatic conveying of solid particles in order to maintain a solids bed with void fraction below 95%. A moving-bed reactor may operate under several flow regimes including settling- or moving packed-bed regime ($U<U_{mf}$), bubbling regime ($U_{mf}<U<U_{mb}$), slugging regime ($U_{mb}<U<U_c$), transition to and turbulent fluidization regime ($U_c<U<U_{tr}$), and fast-fluidization regime ($U>U_{tr}$). These different fluidization regimes have been described in, for example, Kunii, D., Levenspiel, O., Chapter 3 of *Fluidization Engineering*, $2^{nd}$ Edition, Butterworth-Heinemann, Boston, 1991 and Walas, S. M., Chapter 6 of Chemical Process Equipment, Butterworth-Heinemann, Boston, 1990.

As used herein the term "settling bed" means a zone or vessel wherein particulates contact with gas flows such that the superficial gas velocity (U) is below the minimum velocity required to fluidize the solid particles, the minimum fluidization velocity ($U_{mf}$), $U<U_{mf}$ in at least a portion of the reaction zone, and/or operating at a velocity higher than the minimum fluidization velocity while maintaining a gradient in gas and/or solid property (such as, temperature, gas or solid composition, etc.) axially up the reactor bed by using reactor internals to minimize gas-solid back-mixing. Description of the minimum fluidization velocity is given in, for example Chapter 3 of "Fluidization Engineering," D. Kunii and O. Levenspiel, $2^{nd}$ Edition, Butterworth-Heinemann, Boston, 1991 and Chapter 6 of "Chemical Process Equipment," S. M. Walas, Butterworth-Heinemann, Boston, 1990, the entirety of which are incorporated by reference.

As used herein the term "fluidized bed" reactor means a zone or vessel with contacting of solids and gas flows such that the superficial gas velocity (U) is sufficient to fluidize solid particles (i.e., above the minimum fluidization velocity $U_{mf}$) and is below the velocity required for dilute-phase pneumatic conveying of solid particles in order to maintain a solids bed with void fraction below 95%. As used herein the term "cascaded fluid-beds" means a series arrangement of individual fluid-beds such that there can be a gradient in gas and/or solid property (such as, temperature, gas or solid composition, pressure etc.) as the solid or gas cascades from one fluid-bed to another. Locus of minimum fluidization velocity is given in, for example, the Kunii and Walas publications noted above.

As used herein the term "riser" reactor means a zone or vessel (such as, vertical cylindrical pipe) used for net upwards transport of solids in fast-fluidization or pneumatic conveying fluidization regimes. Fast fluidization and pneumatic conveying fluidization regimes are characterized by superficial gas velocities (U) greater than the transport velocity ($U_{tr}$). Fast fluidization and pneumatic conveying fluidization regimes are also described in the Kunii and Walas publications noted above.

As used herein, references to heating by "indirect contact" with combustion gases are meant to include heat transfer across a heat transfer surface and/or use of a heat transfer medium (gas, liquid, or solid) that is heated by the combustion gases and gives up its heat to the catalytic particulate material.

It is to be appreciated that a reaction zone having an inverse temperature profile is a reaction zone in which the inlet reaction temperature to the reaction zone is lower that the process gas outlet reaction temperature, namely the inverse of the temperature profile naturally achieved for an endothermic reaction, such as methane aromatization. Alternately, an inverse temperature profile can mean the temperature profile of a series of catalyst zones, wherein the first (as defined by feed inlet) reaction zone is operated at a lower reaction temperature than is or are the subsequent (as defined by process gas outlet) reaction zone(s), namely the inverse of the temperature profile naturally achieved for an endothermic reaction, This inverse temperature profile can be achieved with countercurrent flow of the feedstock and the particulate dehydrocyclization catalyst by, for example, introducing hot catalyst at the top of the reaction zone so that the catalyst moves downward through the reaction zone, with the reduced temperature catalyst being removed from the bottom of the reaction zone. Feed is introduced at bottom of the reaction zone and flows countercurrent to the catalyst up the reaction zone so that it contacts the hottest portion of the catalyst at the process gas outlet. Alternately, the inverse temperature profile can be achieved by supplying heat along the reactor zone(s).

In one embodiment, the present invention is a process for converting methane to higher hydrocarbons including aromatic hydrocarbons, the process comprising:
a. providing to the reaction zone a hydrocarbon feedstock containing methane;
b. providing a quantity of catalytic material within the reaction zone;
c. maintaining the reaction zone with an inverse temperature profile; and
d. operating the reaction zone under reaction conditions sufficient to convert at least a portion of the methane to a first effluent having the higher hydrocarbon(s).

In a further embodiment, the present invention is a process for converting methane to higher hydrocarbons including aromatic hydrocarbons in two or more reaction zones operated in series, the process comprising:
a. providing a quantity of catalytic material within each reaction zone;
b. providing to a first reaction zone a hydrocarbon feedstock containing methane;
c. transfer at least a portion of the effluent of the first reaction zone to a second reaction zone;
d. maintaining the first reaction zone at a lower average temperature than the second reaction zone; and
e. operating the reaction zones under reaction conditions sufficient to convert at least a portion of the methane to a first effluent having the higher hydrocarbon(s).

Conveniently, the reaction zone(s) may be moving bed or fixed bed reaction zone(s).

Conveniently, the feedstock further comprises at least one of $CO$, $CO_2$, $H_2$, $H_2O$, and/or $O_2$.

Conveniently, the catalytic material may have coke removed by reacting the coke with hydrogen or oxygen; it is preferred that removal with hydrogen is accomplished at pressures of at least 100 kPa, such between about 150 kPa and about 5,000 kPa. Conveniently, when the reaction zone(s) are moving bed(s), a portion of the catalyst is withdrawn from the reaction zone; at least a portion of coke deposited on the catalyst is removed by oxidation; and the catalyst with a reduced level of coke is returned to the reaction zone; or a portion of the catalyst is withdrawn from the reaction zone; at least a portion of coke deposited on the catalyst is removed by reaction with hydrogen to form methane; and the catalyst with a reduced level of coke is returned to the reaction zone.

Alternately, when the reaction zone(s) are fixed bed(s), cyclically the hydrocarbon feed is halted and an oxygen containing stream is instead supplied to the reaction zone so that at least a portion of coke deposited on the catalyst is removed by oxidation; the oxygen containing stream is then halted; and the hydrocarbon feed is restarted; or alternately, cyclically the hydrocarbon feed is halted and a hydrogen containing stream is instead supplied to the reaction zone so that at least a portion of coke deposited on the catalyst is removed by conversion to methane; the hydrogen containing stream is then halted; and the hydrocarbon feed is restarted.

In one embodiment, the reaction conditions in the reaction zone in (b) are non-oxidizing conditions. Conveniently, the reaction conditions in the reaction zone in (b) include a temperature of about 400° C. to about 1200° C., a pressure of about 1 kPa-a to about 1000 kPa-a, and a weight hourly space velocity of about 0.01 $hr^{-1}$ to about 1000 $hr^{-1}$.

In one embodiment, the catalytic material is a dehydrocyclization catalyst comprising a metal or compound thereof on an inorganic support. Conveniently, the catalytic particulate material comprises at least one of molybdenum, tungsten, rhenium, a molybdenum compound, a tungsten compound, a zinc compound, and a rhenium compound on ZSM-5, silica or an aluminum oxide.

Conveniently, the initial catalyzed reaction temperature is less than about 750° C.; preferably less than about 700° C.; alternately less than about 650° C.; and the final catalyzed reaction temperature is greater than about 700° C.; preferably greater than about 800° C.; alternately greater than about 850° C.

Conveniently, sufficient quantity of catalyst is provide so that the % approach to thermodynamic equilibrium conversion of methane to benzene at the reaction zone halfway point (in terms of quantity of catalyst contacted by hydrocarbon) is greater than about 25%; preferably greater than about 50%; most preferably greater than about 75%. Alternately, sufficient quantity of catalyst is provided so that the % approach to thermodynamic equilibrium conversion of methane to benzene at the reaction zone halfway point (in terms of half of the total differential temperature across the reaction zone) is greater than about 25%; preferably greater than about 50%; most preferably greater than about 75%.

Conveniently, the inverse temperature profile in the fixed bed of catalyst is achieved by intermittent direct contact heating with combustion gases or an inert medium heated by the combustion gases. Alternately, the inverse temperature profile in the fixed bed of catalyst is achieved by heat transfer through a heat transfer surface; wherein heat transfer surface is heated by radiative and or conductive heat transfer from combustion. Conveniently, the heat transfer surface is a metal or ceramic. Conveniently, the catalyst is located in one or more tubes in parallel and the tubes are located within a furnace providing heat to maintain the inverse temperature profile. Alternately, the catalyst is located in a vessel with one or more tubes passing through the bed; the tubes conveying combustion gas to maintain the inverse temperature profile. Alternately, when two or more reaction zones are utilized, the temperature staging is achieved in the fixed beds of catalyst by heating of the hydrocarbon stream by heat transfer through a heat transfer surface; the heating of the hydrocarbon stream be carried out between the reaction zones.

In one embodiment, the countercurrent flow of the feedstock and the particulate dehydrocyclization catalyst is arranged to produce an inverse temperature profile in the or each reaction zone, such that, despite the endothermic nature of the dehydrocyclization reaction, the difference between the process gas outlet reaction temperature from the reaction zone and the inlet reaction temperature to the reaction zone is at least +10° C., such as at least +50° C., for example at least +100° C., and even at least +150° C.

In one embodiment, the present invention provides a process for producing aromatic hydrocarbons by contacting a feedstock containing methane, in some embodiments together with $H_2$, $H_2O$, $O_2$, CO and/or $CO_2$, with a particulate dehydrocyclization catalyst in a reaction zone under conditions effective to convert the methane to aromatic hydrocarbons and hydrogen. As the reaction proceeds, coke builds up on the catalyst thereby reducing the activity of the catalyst and hence a portion of the coked catalyst can be continuously or intermittently withdrawn from the reaction zone and passed to a separate regeneration zone, where the coked catalyst is contacted with a hydrogen-containing regeneration gas. Since the dehydrocyclization reaction is endothermic, heat is supplied to the coked catalyst withdrawn from the reaction zone to raise its temperature to the desired regeneration temperature, which is in some embodiments from about 700° C. to about 1200° C., by direct and/or indirect contact with combustion gases produced by combustion of a supplemental fuel. Part of the heated coked catalyst may then be returned to the reaction zone to provide heat to the dehydrocyclization reaction, while the remainder of the heated catalyst is contacted with the hydrogen-containing regeneration gas in the regeneration zone under conditions such that at least part of the coke on the catalyst is converted to methane. The regenerated catalyst is then returned to the reaction zone.

In one embodiment, the regeneration is conducted by withdrawing two or more portions of the coked catalyst from the reaction zone, supplying heat to the catalyst portions and contacting the heated catalyst portions with a hydrogen-containing gas in separate regeneration zones operated under conditions such that the hydrogen partial pressure in at least two of the regeneration zones are different.

Feedstock

Any methane-containing feedstock can be used in the process of the invention but in general the present process is intended for use with a natural gas feedstock. Other suitable methane-containing feedstocks include those obtained from sources such as coal beds, landfills, agricultural or municipal waste fermentation, and/or refinery gas streams.

Methane-containing feedstocks, such as natural gas, typically contain carbon dioxide and ethane in addition to methane. Ethane and other aliphatic hydrocarbons that may be present in the feed can of course be converted to desired aromatics products in the dehydrocyclization step. In addition, as will be discussed below, carbon dioxide can also be converted to useful aromatics products either directly in the dehydrocyclization step or indirectly through conversion to methane and/or ethane in the hydrogen rejection step.

Nitrogen and/or sulfur impurities are also typically present in methane-containing streams may be removed, or reduced to low levels, prior to use of the streams in the process of the invention. In an embodiment, the feed to the dehydrocyclization step contains less than 100 ppm, for example less than 10 ppm, such as less than 1 ppm each of nitrogen and sulfur compounds.

In addition to methane, the feed to the dehydrocyclization step may contain at least one of hydrogen, water, oxygen, carbon monoxide and carbon dioxide in order to assist in coke mitigation. These additives can be introduced as separate co-feeds or can be present in the methane stream, such as, for example, where the methane stream is derived from natural gas containing carbon dioxide. Other sources of carbon dioxide may include flue gases, LNG plants, hydrogen plants, ammonia plants, glycol plants and phthalic anhydride plants.

In one embodiment, the feed to the dehydrocyclization step contains carbon dioxide and comprises about 90 to about 99.9 mol %, such as about 97 to about 99 mol %, methane and about 0.1 to about 10 mol %, such as about 1 to about 3 mol %, $CO_2$. In another embodiment, the feed to the dehydrocyclization step contains carbon monoxide and comprises about 80 to about 99.9 mol %, such as about 94 to about 99 mol %, methane and about 0.1 to about 20 mol %, such as about 1 to about 6 mol %, CO. In a further embodiment, the feed to the dehydrocyclization step contains steam and comprises about 90 to about 99.9 mol %, such as about 97 to about 99 mol %, methane and about 0.1 to about 10 mol %, such as about 1 to about 5 mol %, steam. In yet a further embodiment, the feed to the dehydrocyclization step contains hydrogen and comprises about 80 to about 99.9 mol %, such as about 95 to about 99 mol %, methane and about 0.1 to about 20 mol %, such as about 1 to about 5 mol %, hydrogen.

The feed to the dehydrocyclization step can also contain higher hydrocarbons than methane, including aromatic hydrocarbons. Such higher hydrocarbons can be recycled from the hydrogen rejection step, added as separate co-feeds or can be present in the methane stream, such as, for example, when ethane is present in a natural gas feed. Higher hydrocarbons recycled from the hydrogen rejection step typically include one-ring aromatics and/or paraffins and olefins having predominately 6 or less, such as 5 or less, for example 4 or less, typically 3 or less carbon atoms. In general, the feed to the dehydrocyclization step contains less than 5 wt %, such as less than 3 wt %, of $C_3$+ hydrocarbons.

Dehydrocyclization

In the dehydrocyclization step of the present process, the methane containing feedstock is contacted with a particulate dehydrocyclization catalyst under conditions, normally non-oxidizing conditions and typically reducing conditions, effective to convert the methane to higher hydrocarbons, including benzene and naphthalene. The principal net reactions involved are as follows:

 (Reaction 1)

 (Reaction 2)

 (Reaction 3)

Carbon monoxide and/or dioxide that may be present in the feed improves catalyst activity and stability by facilitating reactions such as:

 (Reaction 4)

but negatively impacts equilibrium by allowing competing net reactions, such as;

 (Reaction 5).

Any dehydrocyclization catalyst effective to convert methane to aromatics can be used in the present process, although generally the catalyst will include a metal component, particularly a transition metal or compound thereof, on an inorganic support. Conveniently, the metal component is present in an amount between about 0.1% and about 20%, such as between about 1% and about 10%, by weight of the total catalyst. Generally, the metal will be present in the catalyst in elemental form or as a carbide species.

Suitable metal components for the catalyst include calcium, magnesium, barium, yttrium, lanthanum, scandium, cerium, titanium, zirconium, hafnium, vanadium, niobium, tantalum, chromium, molybdenum, tungsten, manganese, rhenium, iron, ruthenium, cobalt, rhodium, iridium, nickel, palladium, copper, silver, gold, zinc, aluminum, gallium, silicon, germanium, indium, tin, lead, bismuth and transuranium metals. Such metal components may be present in elemental form or as metal compounds, such as oxides, carbides, nitrides and/or phosphides, and may be employed alone or in combination. Platinum and osmium can also be used as one of the metal component but, in general, are not preferred.

The inorganic support may be either amorphous or crystalline and in particular may be an oxide, carbide or nitride of boron, aluminum, silicon, phosphorous, titanium, scandium, chromium, vanadium, magnesium, manganese, iron, zinc, gallium, germanium, yttrium, zirconium, niobium, molybdenum, indium, tin, barium, lanthanum, hafnium, cerium, tantalum, tungsten, or other transuranium elements. In addition, the support may be a porous material, such as a microporous crystalline material or a mesoporous material. As used herein the term "microporous" refers to pores having a diameter of less than 2 nanometers, whereas the term "mesoporous" refers to pores having a diameter of from 2 to 50 nanometers.

Suitable microporous crystalline materials include silicates, aluminosilicates, titanosilicates, aluminophosphates, metallophosphates, silicoaluminophosphates or their mixtures. Such microporous crystalline materials include materials having the framework types MFI (e.g., ZSM-5 and silicalite), MEL (e.g., ZSM-11), MTW (e.g., ZSM-12), TON (e.g., ZSM-22), MTT (e.g., ZSM-23), FER (e.g., ZSM-35), MFS (e.g., ZSM-57), MWW (e.g., MCM-22, PSH-3, SSZ-25, ERB-1, ITQ-1, ITQ-2, MCM-36, MCM-49 and MCM-56), IWR (e.g., ITQ-24), KFI (e.g., ZK-5), BEA (e.g., zeolite beta), ITH (e.g., ITQ-13), MOR (e.g., mordenite), FAU (e.g., zeolites X, Y, ultrastabilized Y and dealuminized Y), LTL (e.g., zeolite L), IWW (e.g., ITQ-22), VFI (e.g., VPI-5), AEL (e.g., SAPO-11), AFI (e.g., ALPO-5) and AFO (SAPO-41), as well as materials such as MCM-68, EMM-1, EMM-2, ITQ-23, ITQ-24, ITQ-25, ITQ-26, ETS-2, ETS-10, SAPO-17, SAPO-34 and SAPO-35. Suitable mesoporous materials include MCM-41, MCM-48, MCM-50, FSM-16 and SBA-15.

Examples of preferred catalysts include molybdenum, tungsten, zinc, rhenium and compounds and combinations thereof on ZSM-5, silica or alumina.

The metal component can be dispersed on the inorganic support by any means well known in the art such as co-precipitation, incipient wetness, evaporation, impregnation, spray-drying, sol-gel, ion-exchange, chemical vapor deposition, diffusion and physical mixing. In addition, the inorganic support can be modified by known methods, such as, for example, steaming, acid washing, caustic washing and/or treatment with silicon-containing compounds, phosphorus-containing compounds, and/or elements or compounds of Groups 1, 2, 3 and 13 of the Periodic Table of Elements. Such modifications can be used to alter the surface activity of the support and hinder or enhance access to any internal pore structure of the support.

In some embodiments, a non-catalytic particulate material may be supplied to the dehydrocyclization reaction in addition to the catalytic particulate material. The non-catalytic particulate material may be used as a material to transport energy (heat) into the system and/or to fill space as required providing the required hydrodynamic environment. The non-catalytic particulate material may form particulates without a binder or may be bound with an inorganic binder such as clay, silica, alumina, zirconia, or other metal oxide used to help maintain the physical integrity of the particles. Preferably the particles are of a substantially spherical shape. Examples of suitable non-catalytic particulate material are low surface area silica, alumina, ceramics, and silicon carbide.

The dehydrocyclization step is conducted by contacting the methane-containing feedstock with the particulate dehydrocyclization catalyst in one or more fixed bed, moving bed or fluidized bed reaction zones. Generally, the feedstock is contacted in the or each reaction zone with a moving bed of dehydrocyclization catalyst, wherein the feedstock flows countercurrent to the direction of movement of the dehydrocyclization catalyst. In one embodiment, the or each reaction zone comprises a settling bed reactor, by which is meant a vertically disposed reactor in which particulate catalyst enters at or near the top of the reactor and flows under gravity to form a catalyst bed, while the feed enters the reactor at or near the base of the reactor and flows upwardly through the catalyst bed.

The movement of the dehydrocyclization catalyst in the reaction zone is substantially free of fluidization in the settling bed embodiment. The term "substantially free of fluidization" as used herein means that the average gas flowing velocity in the reactor is lower than the minimum fluidizing velocity. The term "substantially free of fluidization" as used herein also means that the average gas flowing velocity in the reactor is less than 99%, such as less than 95%, typically less than 90%, even less than 80% of the minimum fluidization velocity. Where the or each reaction zone is operated as a settling bed, the particulate catalytic material and/or any particulate non-catalytic material has an average particle size from about 0.1 mm to about 100 mm, such as from about 1 mm to about 5 mm, and for example from about 2 mm to about 4 mm. In some embodiments, at least 90 wt. % of the particulate catalytic material and/or at least 90 wt. % of the particulate non-catalytic material has an particle size from about 0.1 mm to about 100 mm, such as from about 1 mm to about 5 mm, for example from about 2 mm to about 4 mm.

In an alternative embodiment, the dehydrocyclization reaction is conducted in a plurality of series-connected fluidized bed reactors in which particulate catalyst is cascaded in one direction from one reactor to the next adjacent reactor in the series, while the feed is passed through and between the reactors in the opposite direction. Wherein each reaction zone is operated as a fluidizing bed, the catalytic particulate material and/or any non-catalytic particulate material has an average particle size from about 0.01 mm to about 10 mm, such as from about 0.05 mm to about 1 mm, and for example from about 0.1 mm to about 0.6 mm. In some embodiments, at least 90 wt. % of the catalytic particulate material and/or at least 90 wt. % of the non-catalytic particulate material have particle size from about 0.01 mm to about 10 mm, such as from about 0.05 to about 1 mm, and for example from about 0.1 to about 0.6 mm.

Typically, the mass ratio of the flowrate of the catalytic particulate material plus any non-catalytic particulate material over the flowrate of the hydrocarbon feedstock in the or each dehydrocyclization reaction zone is from about 1:1 to about 100:1, such as from about 1:1 to about 40:1, for example from about 5:1 to 20:1.

The dehydrocyclization reaction is endothermic and hence the temperature in each dehydrocyclization reaction zone will tend to decrease from a maximum temperature to a minimum temperature as the reaction proceeds. Suitable conditions for the dehydrocyclization step include a maximum temperature of about 700° C. to about 1200° C., such as about 800° C. to about 950° C. and a minimum temperature of about 400° C. to about 800° C., such as about 500° C. to about 700° C. However, as will be discussed below, heat is supplied to the dehydrocyclization reaction to reduce the temperature drop during the reaction and hence in some configurations it is possible to reduce the difference between the maximum and minimum temperatures to essentially zero. Alternatively, by supplying heated catalyst to the dehydrocyclization reaction, it is possible to produce an inverse temperature profile; that is with the process gas outlet reaction temperature being greater than the process gas inlet reaction temperature.

In one embodiment, the countercurrent flow of the feedstock and the particulate dehydrocyclization catalyst is arranged to produce an inverse temperature profile across dehydrocyclization reaction system, such that, despite the endothermic nature of the dehydrocyclization reaction, the difference between the reaction temperature of the gaseous effluent at the outlet from the dehydrocyclization reaction system and the reaction temperature of the methane-containing feed at the inlet to the dehydrocyclization reaction system is at least +10° C., such as at least +50° C., for example at least +100° C., and even at least +150° C.

In any event, since the dehydrocyclization reaction is endothermic, the catalytic particulate material enters the dehydrocyclization reaction system at a first, high temperature, typically about 800° C. to about 1200° C., such as about 900° C. to about 1100° C., and exits the reaction system at a second lower temperature, typically about 500° C. to about 800° C., such as about 600° C. to about 700° C. The total temperature difference of the catalytic particulate material across the reaction zones is at least 100° C.

Other conditions used in the dehydrocyclization reaction generally include a pressure of about 1 kPa to about 1000 kPa, such as about 10 to about 500 kPa, for example about 50 kPa to about 200 kPa and a weight hourly space velocity of about 0.01 to about 1000 hr-1, such as about 0.1 to about 500 hr$^{-1}$, for example about 1 to about 20 hr$^{-1}$. Conveniently, the dehydrocyclization step is conducted in the absence of $O_2$.

The major components of the effluent from the dehydrocyclization step are hydrogen, benzene, naphthalene, carbon monoxide, ethylene, and unreacted methane. Typically, the effluent contains at least 5 wt. %, such as at least 10 wt. %, for example at least 20 wt. %, conveniently at least 30 wt. %, more aromatic rings than the feed.

The benzene and naphthalene are separated from the dehydrocyclization effluent, for example, by solvent extraction followed by fractionation, and can be recovered as a product stream. However, as will be discussed below, at least part of these aromatic components can be submitted to an alkylation step, before or after product recovery, to produce higher value materials, such as xylenes. Moreover, as will be discussed below, the present process utilizes the hydrogen generated as a by-product of the dehydrocyclization reaction and in particular converts at least part of the hydrogen to higher value products.

Catalyst Regeneration

The dehydrocyclization reaction tends to deposit coke on the catalyst and hence, to maintain the activity of the dehydrocyclization catalyst, at least part of the catalyst can be continuously or intermittently regenerated. This is typically achieved by withdrawing a portion of the catalyst from the or each reaction zone, either on an intermittent, or a continuous basis, and is transferred to a separate regeneration zone. In the regeneration zone, the coked dehydrocyclization catalyst is contacted with a hydrogen-containing gas under conditions effective to convert at least a portion of the carbonaceous material thereon to methane. Generally, the hydrogen-containing gas does not contain significant quantities of methane or other hydrocarbons; typically with the hydrocarbon content being less than 20 mol %, such as less than 10 mol %, for example less than 2 mol %. In one embodiment, the hydrogen required for the regeneration is obtained at least in part from the hydrogen-containing effluent from the dehydrocyclization reaction.

Conveniently, the regeneration conditions comprise a temperature from about 700° C. to about 1200° C., such as from about 800° C. to about 1000° C., such as about 850° C. to about 950° C. and a pressure of at least 100 kPa, such between about 150 kPa and about 5000 kPa. Generally, however, the coked dehydrocyclization catalyst removed from the or each reaction zone will be at a lower temperature than the optimum for regeneration and hence the removed catalyst is initially heating to a desired regeneration temperature by direct and/or indirect contact with combustion gases produced by combustion of a supplemental fuel. The heating is conducted in a heating zone which may be in the same vessel as the regeneration zone or which may be in a separate vessel from the regeneration zone.

By "supplemental source of fuel" is meant that the source fuel is physically separate from the catalyst and hence is not, for example, coke generated on the catalyst as a by-product of the dehydrocyclization reaction. Typically, the supplemental source of fuel comprises a hydrocarbon, such as methane, and in particular a suitable fuel source is the natural gas used as the feedstock to the process. Conveniently, an oxygen-lean atmosphere is maintained in the heating zone so that burning the hydrocarbon fuel to heat the first catalyst portion produces synthesis gas, which can then be used to generate additional hydrocarbon product and/or fuel. In addition, in the case of direct heat transfer to the dehydrocyclization catalyst, the use of an oxygen-lean atmosphere inhibits oxidation of metal carbides present in the catalyst and minimizes the average steam partial pressure thereby reducing catalyst hydrothermal aging.

Alternatively, a suitable supplemental fuel source is hydrogen and, in particular, part of the hydrogen generated as a by-product of the aromatization reaction.

Where the dehydrocyclization catalyst is heated directly, the coked catalyst withdrawn from the reaction zone is conveniently contacted directly with the burning source of fuel in the heating zone. Alternatively, the source of fuel is burned in a separate combustion zone and the combustion gases generated in the combustion zone are fed to the heating zone to heat the catalyst. Alternatively, the dehydrocyclization catalyst can be heated by indirect heat exchange such as, for example, by using the combustion gases to heat an inert medium (gas, liquid, or solid) or a heat transfer surface and then contacting the coked catalyst with the heated inert medium or heat transfer surface.

In one practical embodiment, the heating zone is elongated and the coked catalyst is passed through the heating zone from an inlet at or adjacent one end of the heating zone to an outlet at or adjacent the other end of the heating zone, with heat being applied to first catalyst portion at a plurality of locations spaced along the length of the heating zone. In this way, the heat input to the catalyst can be distributed along the length of the heating zone thereby minimizing catalyst surface temperatures and internal gradients.

Where the first catalyst portion is heated by direct contact with the burning source of fuel in the heating zone, gradual heating of the catalyst can be achieved by supplying substantially all of the supplemental fuel to the inlet end of the heating zone and then supplying the oxygen-containing gas incrementally to the heating zone at the plurality of spaced locations along the length of heating zone. Alternatively, substantially all of the oxygen-containing gas required to burn the supplemental fuel can be supplied to the inlet end of the heating zone and the supplemental fuel supplied incrementally to the heating zone at the plurality of spaced locations.

Where the first catalyst portion is heated by direct contact with hot combustion gases generated in a separate combustion zone, gradual heating of the catalyst can be achieved by supplying the hot combustion gases to the plurality of spaced locations along the length of heating zone.

In one embodiment, the heating zone is a riser and the first catalyst portion is passed upwardly through the riser during the reheating step. In practice, the heating zone may include a plurality of risers connected in parallel. Alternatively, the heating zone can include a moving bed of the catalyst.

In one embodiment, the coked dehydrocyclization catalyst removed from the reaction zone is divided into at least two portions, which are heated as described above and then fed to separate regeneration zones operated at different pressures. For example, one regeneration zone is operated at a pressure of at least 100 kPa, such between about 150 kPa and about 700 kPa, as described above, whereas the other regeneration zone is operated at a pressure of at least 500 kPa, such between about 1000 kPa and about 5000 kPa. Thus, it has been found, as shown in the Examples, that higher pressure regeneration provides faster removal of coke as well as removal of more refractory coke. However it has also been determined that it will require more expensive hardware to enable removal of coke at higher pressures. For this reason, there may be advantage in removing a portion of the coke at a lower hydrogen partial pressure in less expensive equipment and removing a further portion of the coke at higher hydrogen partial pressure in more expensive equipment.

The or each regeneration zone may be a reactor operated as a fluidized bed, an ebulating bed, a settling bed, a riser reactor or a combination thereof. In practice, each regeneration zone may include a plurality of reactors, such as a plurality of riser reactors connected in parallel or a plurality of reactors connected in series such as a riser reactor followed by a settling bed. After regeneration the catalyst is returned to reaction zone.

In an alternative embodiment, and particularly where the dehydrocyclization reaction is conducted in a fixed bed reactor, the regeneration can be conducted without removal of the catalyst from the reaction zone, by temporarily discontinuing the supply of methane-containing feedstock to the reaction zone, heating the reaction zone to a regeneration temperature of about 700° C. to about 1200° C. by direct and/or indirect contact with combustion gases produced by combustion of a supplemental fuel, regenerating the particulate catalytic material with a hydrogen-containing gas, and then re-establishing the supply of methane-containing feedstock to the reaction zone. It is to be appreciated that heating the reaction zone to the regeneration temperature can be affected before the supply of methane-containing feedstock is discontinued.

Catalyst Reheating

Since the dehydrocyclization reaction is endothermic, it is necessary to supply heat to the reaction. In the present process, this is conveniently achieved by withdrawing part of the catalyst from the reaction zone, either on an intermittent or a continuous basis, supplying heat to the catalyst and then returning the heated catalyst back to the reaction zone. Since the hydrogen regeneration step described above also involves heating the catalyst and then recycling the heated regenerated catalyst back to the reaction zone, one possible route for supplying heat to the dehydrocyclization reaction is by means of the regeneration process.

Alternatively, some or all of the heat required to maintain the dehydrocyclization reaction can be supplied by a separate catalyst reheating step. In this embodiment, part of the catalyst withdrawn for the reaction zone is transferred to a separate heating zone, where again the catalyst is heated by direct or indirect contact with hot combustion gases generated by burning a supplemental source of fuel. The heated catalyst is then returned to the reaction zone with or without undergoing hydrogen regeneration.

Alternately, for fixed bed applications, the catalyst may be heated by cyclically stopping the flow of hydrocarbon feed and passing hot gasses over the catalyst bed. These hot gasses may be combustion products or inert gas. Preferentially the hot gas is passed through the catalyst bed in the direction opposite to the flow of the hydrocarbon feed so as to establish an inverse temperature profile in the catalyst bed.

Catalyst Recarburizing

It will be appreciated that heating the dehydrocyclization catalyst for the purposes of regeneration and/or for heat transfer back the dehydrocyclization reaction may subject the catalyst to high temperature oxidizing conditions, especially where catalyst heating involves direct contact with hot combustion gases. As a result, metals, such as rhenium, tungsten or molybdenum, present in the dehydrocyclization catalyst may be converted during the heating step from their catalytically active elemental or carbide form to an oxide species. Thus, before being returned to the reaction zone, the regenerated and/or reheated catalyst may be transferred to a catalyst treatment zone separate from the regeneration zone, the heating zone and the reaction zone, where the catalyst is contacted with a carburizing gas containing at least one hydrocarbon selected from methane, ethane, propane, butane, isobutene, hexane, benzene and naphthalene. In some cases, the carburizing gas may also contain at least one of $CO_2$, CO, $H_2$, $H_2O$ and inert diluents. Alternatively, the carburizing gas may be a mixture of hydrogen and at least one of CO and $CO_2$. Moreover, it may be desirable to contact the catalyst sequentially with a plurality of different carburizing gases, each comprising a hydrocarbon selected from methane, ethane, propane, butane, isobutene, hexane, benzene and naphthalene or a mixture of hydrogen and at least one of CO and $CO_2$.

To avoid damage to the catalyst, the carburization process is controlled so that the maximum temperature in the catalyst treatment zone is less than the maximum temperature in the dehydrocyclization reaction zone, although typically the maximum carburization temperature is higher than the maximum temperature reached in an oxidative regeneration zone. Generally the maximum temperature in the catalyst treatment zone is from about 400° C. to about 1100° C., such as from about 500° C. to about 900° C., with the minimum temperature being between 300° C. and 500° C. Typically, the catalyst treatment zone is operated at pressures between 10 and 100 psi (69 and 690 kPa), such as between 15 and 60 psi (103 and 414 kPa). Generally, the average residence time of catalyst particles in the catalyst treatment zone will be between 0.1 and 100 minutes, for example between 1 and 20 minutes. Under these conditions, the carburizing gas reacts with metal oxide species on the catalyst to return the metal to its catalytically active elemental or carbidic form. In addition, the carburizing gas can react with active surface sites on the catalyst support to decrease their tendency to generate coke in the dehydroaromatization reaction zone.

To maintain the temperature required for carburization of the regenerated catalyst, heat can supplied to the catalyst and/or the carburizing gas prior to or during the carburization step. For example heat can be supplied to the catalyst by indirect heating, by contacting with hot flue gas from the reaction zone or the heating zone, by contacting with the hot gaseous effluent from the carburization process, or by mixing with heated catalyst from the heating zone. Heat is conveniently supplied to the carburization gas by means of an external furnace or heat exchanger or by with heated catalyst from the heating zone.

The catalyst treatment zone may be operated as a fluidized bed reactor, ebulating bed reactor, settling bed reactor, riser reactor or circulating riser reactor. In one embodiment, the catalyst treatment zone comprises a settling bed reactor. Alternatively, the catalyst treatment zone comprises a single fluidized bed reactor with internal baffles to prevent back-mixing or a plurality of fluidized bed reactors in series with the regenerated catalyst being cascaded between adjacent reactors. In any event, contact in the catalyst treatment zone is facilitated by arranging that the regenerated catalyst and the carburizing gas flow in opposite directions in the catalyst treatment zone. Employing such a countercurrent flow, a temperature profile may be developed in the catalyst treatment zone such that carburization of the regenerated catalyst initially occurs at a low temperature but the carburization temperature increases as the catalyst flows through the bed.

In some cases, it may be desirable that the heated unregenerated catalyst is initially contacted with a $H_2$-rich stream to partially or fully reduce the metal component of the catalyst prior to the carburization step. It may also be desirable to subject the carburized catalyst to post treatment with $H_2$ and/or $CO_2$ to strip off any excess carbon that may have been deposited on the catalyst by the carburization step.

In practice, as the dehydrocyclization reaction proceeds, fresh dehydrocyclization catalyst will be added to the process either to make up for catalyst lost by mechanical attrition or deactivation and, although there are multiple means of addition of fresh catalyst, to avoid damage to the catalyst, it is generally desirable to add fresh catalyst to a region of the process that is operating at a temperature below the maximum temperature in each dehydrocyclization reaction zone. In one embodiment, fresh dehydrocyclization catalyst is added to the process by introduction into the catalyst treatment zone, whereby the fresh catalyst is contacted with the carburizing gas prior to transfer to the reaction zone for contact with the methane-containing feed. In another, embodiment the catalyst may be added to the lower temperature regions of a reactor system with an inverse temperature profile.

Materials of Construction for Reactor Vessels, Internals, and Heat Transfer Surfaces Conveniently, in the process for converting methane to higher hydrocarbons including aromatic hydrocarbons, the process comprising contacting a feed containing methane with a dehydrocyclization catalyst in a reaction zone under conditions effective to convert the methane to aromatic hydrocarbons, wherein the reaction zone is contained within a reactor and wherein the reactor or an internal component of the reactor has at least one surface that is chemically exposed to the feed and is formed from a refractory material that exhibits a carbon uptake (mass of carbon absorbed per unit of exposed metal surface area) of less than 25 $g/m^2$, preferably 15 $g/m^2$ and most preferably 10 $g/m^2$, when exposed to mixture of 50 vol % methane and 50 vol % $H_2$ at 900° C. for 168 hours.

In a further aspect, in the process for converting methane to higher hydrocarbons including aromatic hydrocarbons, the process comprising contacting a feed containing methane with a dehydrocyclization catalyst in a reaction zone under conditions effective to convert the methane to aromatic hydrocarbons, wherein the reaction zone is contained within a reactor and wherein the reactor or an internal component of the reactor has at least one surface that is chemically exposed to the feed and that is formed from a refractory metal or alloy that comprises, or is capable of forming and/or maintaining under the conditions, a continuous oxide or carbide layer stable under the conditions.

Conveniently, at least one surface is formed from a refractory alloy containing at least 2 weight % of at least one of aluminum, magnesium or cerium.

Conveniently, at least one surface is formed of molybdenum, tungsten, chromium and/or niobium.

Conveniently, the at least one surface is chemically exposed to the feed through a refractory, abrasion resistant coating, typically comprising at least one of a ceramic, phosphide, nitride, carbide, and oxide.

In yet a further aspect, in the process for converting methane to higher hydrocarbons including aromatic hydrocarbons, the process comprising contacting a feed containing methane with a dehydrocyclization catalyst in a reaction zone under conditions effective to convert the methane to aromatic hydrocarbons, wherein the reaction zone is contained within a reactor and wherein the reactor or an internal component of the reactor has at least one surface that is chemically exposed to the feed and that is formed from a refractory alloy containing at least 2 weight % of at least one of aluminum, magnesium or cerium.

Conveniently, at least one surface is formed from an iron-based alloy. Conveniently, the iron-based alloy comprises chromium, such as between about 15 and about 25 weight % chromium, and at least 2 weight %, such as between about 4 and about 6 weight %, aluminum in addition to iron.

Conveniently, at least one surface is formed from a nickel-based alloy. Conveniently, the nickel-based alloy comprises chromium, such as between about 15 and about 30 weight % chromium, and at least 2 weight %, such as between about 3 and about 5 weight %, aluminum in addition to nickel.

As used herein the terms "iron-based alloy" and "nickel-based alloy" means an alloy containing greater than 50 weight % of iron and nickel respectively.

The present invention provides a process for producing aromatic hydrocarbons by contacting a feedstock containing methane, typically together with $H_2$, CO and/or $CO_2$, with a dehydrocyclization catalyst in a reaction zone under conditions effective to convert the methane to aromatic hydrocarbons and hydrogen. The reaction zone maybe contained within a reactor and the reactor or an internal component of the reactor may have at least one surface that is chemically exposed to the feed and that is formed from a refractory material that exhibits a carbon uptake (mass of carbon absorbed per unit of exposed metal surface area) of less than 25 $g/m^2$, preferably 15 $g/m^2$ and most preferably 10 $g/m^2$, when exposed to mixture of 50 vol % methane and 50 vol % $H_2$ at 900° C. for 168 hours. Typically, the least one surface is formed from a refractory alloy containing a metal constituent, having or being capable of forming and/or maintaining under the conditions, a stable, continuous oxide layer and/or from a refractory metal or alloy capable of forming a stable, continuous carbide layer under the conditions.

Refractory materials that are resistant to carburization when contacted with feedstock containing methane for producing aromatic hydrocarbons at high temperatures have been identified. These refractory materials, which may be directly exposed to process gases and conditions, can be used as bulk metal alloys or as cladding to conventional alloys where the carburization resistance of the conventional alloys is improved due to the high carburization resistance of its surface cladding.

When the surface of a metal alloy is exposed to hydrocarbon gases at high temperatures, the metal surface is able to catalyze the conversion of hydrocarbons to coke leading to significant coke build-up. Carbide-forming metals (such as, molybdenum, tungsten, etc.) that are resistant to surface coking due to the formation of a metal carbide surface layer under reductive coupling conditions have been identified. These carbide-forming metals can be used as bulk metallurgy or as surface coatings or as cladding to conventional alloys to provide improved coking/carburization resistance.

Where the surface will be exposed to erosive environments, such as high velocity gases and/or moving catalysts particles, it may be desirable to provide the surface with a refractory, abrasion resistant coating, typically comprising at least one of a ceramic, phosphide, nitride, carbide, and oxide. This is because exposure of the alloy surface to high velocity gases and/or moving catalyst particles can erode the protective metal oxide or carbide layer present on its surface, which may lead to increased rate of carburization of the bulk alloy. Moreover, surface erosion can preferentially deplete the metal alloy of its constituent metal that forms the protective layer (such as aluminum), thereby making it harder to repair defects in the surface protective oxide/carbide layer under process conditions. In addition to mitigating surface erosion, these abrasion-resistant coatings can serve as thermal insulators which, in some applications, can lower surface alloy temperatures when used in conjunction with cooling systems. Since the underlying surface is resistant to carburization, there is no requirement that the abrasive coating is also resistant to carbon ingress. Examples of reactor surfaces that are desirably provided with abrasion resistant coatings are the operating surfaces of reactor internals, such as gas distributors, slide valves and cyclones.

Hydrogen Management

Since hydrogen is a major component of the dehydrocyclization effluent, after recovery of the aromatic products, the effluent may be subjected to a hydrogen rejection step to reduce the hydrogen content of the effluent before the unreacted methane is recycled to the dehydrocyclization step and to maximize feed utilization. Typically the hydrogen rejection step comprises reacting at least part of the hydrogen in the dehydrocyclization effluent with an oxygen-containing species, such as CO and/or $CO_2$, to produce water and a second effluent stream having a reduced hydrogen content compared with the first (dehydrocyclization) effluent stream. Suitable hydrogen rejection processes are described below and in our copending PCT Application Ser. No. PCT/US2005/044042, filed on Dec. 2, 2005.

Conveniently, the hydrogen rejection step includes (i) methanation and/or ethanation, (ii) a Fischer-Tropsch process, (iii) synthesis of $C_1$ to $C_3$ alcohols, particularly methanol, and other oxygenates, (iv) synthesis of light olefins, paraffins and/or aromatics by way of a methanol or dimethyl ether intermediate and/or (v) selective hydrogen combustion. These steps may be employed sequentially to gain the greatest benefit; for example Fischer-Tropsch may first be employed to yield a $C_2$+ enriched stream followed by methanation to achieve high conversion of the $H_2$.

Typically, as described below, the hydrogen rejection step will generate hydrocarbons, in which case, after separation of the co-produced water, at least portion of the hydrocarbons are conveniently recycled to the dehydrocyclization step. For example, where the hydrocarbons produced in the hydrogen rejection step comprise paraffins and olefins, the portion recycled to the dehydrocyclization step conveniently comprises, paraffins or olefins with 6 or less carbon atoms, such as 5 or less carbon atoms, for example 4 or less carbon atoms or 3 or less carbon atoms. Where, the hydrocarbons produced in the hydrogen rejection step comprise aromatics, the portion recycled to the dehydrocyclization step conveniently comprises single ring aromatic species.

Alternately hydrogen may be separated from the hydrocarbon stream utilizing physical separation technologies such as cryogenic distillation, pressure swing adsorption, thermal swing adsorption, and or membrane systems. It may be desirable to physically separate the hydrogen when there is a useful disposition for a hydrogen enriched stream.

Methanation/Ethanation

In one embodiment the hydrogen rejection step comprises reaction of at least part of the hydrogen in the dehydrocyclization effluent with carbon dioxide to produce methane and/or ethane according to the following net reactions:

$$CO_2 + 4H_2 \leftrightarrow CH_4 + 2H_2O \qquad \text{(Reaction 6)}$$

$$2CO_2 + 7H_2 \leftrightarrow C_2H_6 + 4H_2O \qquad \text{(Reaction 7)}$$

The carbon dioxide employed is conveniently part of a natural gas stream and typically the same natural gas stream used as the feed to the dehydrocyclization step. Where the carbon dioxide is part of a methane-containing stream, the $CO_2:CH_4$ of the stream is conveniently maintained between about 1:1 and about 0.1:1. Mixing of the carbon dioxide-containing stream and the dehydrocyclization effluent is conveniently achieved by supplying the gaseous feeds to the inlet of a jet ejector.

The hydrogen rejection step to produce methane or ethane normally employs a $H_2:CO_2$ molar ratio close to the stoichiometric proportions required for the desired Reaction 6 or Reaction 7, although small variations can be made in the stoichiometric ratio if it is desired to produce a $CO_2$-containing or $H_2$-containing second effluent stream. The hydrogen rejection step to produce methane or ethane is conveniently effected in the presence of a bifunctional catalyst comprising a metal component, particularly a transition metal or compound thereof, on an inorganic support. Suitable metal components comprise copper, iron, vanadium, chromium, zinc, gallium, nickel, cobalt, molybdenum, ruthenium, rhodium, palladium, silver, rhenium, tungsten, iridium, platinum, gold, gallium and combinations and compounds thereof. The inorganic support may be an amorphous material, such as silica, alumina or silica-alumina, or like those listed for the dehydroaromatization catalyst. In addition, the inorganic support may be a crystalline material, such as a microporous or mesoporous crystalline material. Suitable porous crystalline materials include the aluminosilicates, aluminophosphates and silicoaluminophosphates listed above for the dehydrocyclization catalyst.

The hydrogen rejection step to produce methane and/or ethane can be conducted over a wide range of conditions including a temperature of about 100° C. to about 900° C., such as about 150° C. to about 500° C., for example about 200° C. to about 400° C., a pressure of about 200 kPa to about 20,000 kPa, such as about 500 to about 5000 kPa and a weight hourly space velocity of about 0.1 to about 10,000 $hr^{-1}$, such as about 1 to about 1,000 $hr^{-1}$. $CO_2$ conversion levels are typically between 20 and 100% and conveniently greater than 90%, such as greater than 99%. This exothermic reaction may be carried out in multiple catalyst beds with heat removal between beds. In addition, the lead bed(s) may be operated at higher temperatures to maximize kinetic rates and the tail beds(s) may be operated at lower temperatures to maximize thermodynamic conversion.

The main products of the reaction are water and, depending on the H$_2$:CO$_2$ molar ratio, methane, ethane and higher alkanes, together with some unsaturated C$_2$ and higher hydrocarbons. In addition, some partial hydrogenation of the carbon dioxide to carbon monoxide is preferred. After removal of the water, the methane, carbon monoxide, any unreacted carbon dioxide and higher hydrocarbons can be fed directly to the dehydrocyclization step to generate additional aromatic products.

Fischer-Tropsch Process

In another embodiment the hydrogen rejection step comprises reaction of at least part of the hydrogen in the dehydrocyclization effluent with carbon monoxide according to the Fischer-Tropsch process to produce C$_2$ to C$_5$ paraffins and olefins.

The Fischer-Tropsch process is well known in the art, see for example, U.S. Pat. Nos. 5,348,982 and 5,545,674 incorporated herein by reference. The process typically involves the reaction of hydrogen and carbon monoxide in a molar ratio of about 0.5:1 to about 4:1, such as about 1.5:1 to about 2.5:1, at a temperature of about 175° C. to about 400° C., such as about 180° C. to about 240° C. and a pressure of about 1 to about 100 bar (100 to 10,000 kPa), such as about 10 to about 40 bar (1,000 to 4,000 kPa), in the presence of a Fischer-Tropsch catalyst, generally a supported or unsupported Group VIII, non-noble metal, e.g., Fe, Ni, Ru, Co, with or without a promoter, e.g. ruthenium, rhenium, hafnium, zirconium, titanium. Supports, when used, can be refractory metal oxides such as Group IVB, i.e., titania, zirconia, or silica, alumina, or silica-alumina. In one embodiment, the catalyst comprises a non-shifting catalyst, e.g., cobalt or ruthenium, especially cobalt, with rhenium or zirconium as a promoter, especially cobalt and rhenium supported on silica or titania, generally titania.

In another embodiment, the hydrocarbon synthesis catalyst comprises a metal, such as Cu, Cu/Zn or Cr/Zn, on the ZSM-5 and the process is operated to generate significant quantities of single-ring aromatic hydrocarbons. An example of such a process is described in *Study of Physical Mixtures of Cr$_2$O$_3$-ZnO and ZSM-5 Catalysts for the Transformation of Syngas into Liquid Hydrocarbons* by Jose Erena; Ind. Eng. Chem Res. 1998, 37, 1211-1219, incorporated herein by reference.

The Fischer-Tropsch liquids, i.e., C$_5$+, are recovered and light gases, e.g., unreacted hydrogen and CO, C$_1$ to C$_3$ or C$_4$ and water are separated from the heavier hydrocarbons. The heavier hydrocarbons can then be recovered as products or fed to the dehydrocyclization step to generate additional aromatic products.

The carbon monoxide required for the Fischer-Tropsch reaction can be provided wholly or partly by the carbon monoxide present in or cofed with the methane-containing feed and generated as a by-product in the dehydrocyclization step. If required, additional carbon monoxide can be generated by feeding carbon dioxide contained, for example, in natural gas, to a shift catalyst whereby carbon monoxide is produced by the reverse water gas shift reaction:

CO$_2$+H$_2$↔CO+H$_2$O  (Reaction 8)

and by the following reaction:

CH$_4$+H$_2$O↔CO+3H$_2$

Alcohol Synthesis

In a further embodiment the hydrogen rejection step comprises reaction of at least part of the hydrogen in the dehydrocyclization effluent with carbon monoxide to produce C$_1$ to C$_3$ alcohols, and particularly methanol. The production of methanol and other oxygenates from synthesis gas is also well-known and is described in, for example, in U.S. Pat. Nos. 6,114,279; 6,054,497; 5,767,039; 5,045,520; 5,254,520; 5,610,202; 4,666,945; 4,455,394; 4,565,803; 5,385,949, the descriptions of which are incorporated herein by reference. Typically, the synthesis gas employed has a molar ratio of hydrogen (H$_2$) to carbon oxides (CO+CO$_2$) in the range of from about 0.5:1 to about 20:1, such as in the range of from about 2:1 to about 10:1, with carbon dioxide optionally being present in an amount of not greater than 50% by weight, based on total weight of the syngas.

The catalyst used in the methanol synthesis process generally includes an oxide of at least one element selected from the group consisting of copper, silver, zinc, boron, magnesium, aluminum, vanadium, chromium, manganese, gallium, palladium, osmium and zirconium. Conveniently, the catalyst is a copper based catalyst, such as in the form of copper oxide, optionally in the presence of an oxide of at least one element selected from silver, zinc, boron, magnesium, aluminum, vanadium, chromium, manganese, gallium, palladium, osmium and zirconium. Conveniently, the catalyst contains copper oxide and an oxide of at least one element selected from zinc, magnesium, aluminum, chromium, and zirconium. In one embodiment, the methanol synthesis catalyst is selected from the group consisting of: copper oxides, zinc oxides and aluminum oxides. More preferably, the catalyst contains oxides of copper and zinc.

The methanol synthesis process can be conducted over a wide range of temperatures and pressures. Suitable temperatures are in the range of from about 150° C. to about 450° C., such as from about 175° C. to about 350° C., for example from about 200° C. to about 300° C. Suitable pressures are in the range of from about 1,500 kPa to about 12,500 kPa, such as from about 2,000 kPa to about 10,000 kPa, for example 2,500 kPa to about 7,500 kPa. Gas hourly space velocities vary depending upon the type of process that is used, but generally the gas hourly space velocity of flow of gas through the catalyst bed is in the range of from about 50 hr$^{-1}$ to about 50,000 hr$^{-1}$, such as from about 250 hr$^{-1}$ to about 25,000 hr$^{-1}$, for example from about 500 hr$^{-1}$ to about 10,000 hr$^{-1}$. This exothermic reaction may be carried out in either fixed or fluidized beds, including multiple catalyst beds with heat removal between beds. In addition, the lead bed(s) may be operated at higher temperatures to maximize kinetic rates and the tail beds(s) may be operated at lower temperatures to maximize thermodynamic conversion.

The resultant methanol and/or other oxygenates can be sold as a separate product, can be used to alkylate the aromatics generated in the dehydrocyclization step to higher value products, such as xylenes, or can be used as a feedstock for the production of lower olefins, particularly ethylene and propylene. The conversion of methanol to olefins is a well-known process and is, for example, described in U.S. Pat. No. 4,499,327, incorporated herein by reference.

Selective Hydrogen Combustion

In yet another embodiment, the hydrogen rejection step comprises selective hydrogen combustion, which is a process in which hydrogen in a mixed stream is reacted with oxygen to form water or steam without substantially reacting hydrocarbons in the stream with oxygen to form carbon monoxide, carbon dioxide, and/or oxygenated hydrocarbons. Generally, selective hydrogen combustion is carried out in the presence of an oxygen-containing solid material, such as a mixed metal oxide, that will release a portion of the bound oxygen to the hydrogen.

One suitable selective hydrogen combustion process is described in U.S. Pat. No. 5,430,210, incorporated herein by reference, and comprises contacting at reactive conditions a first stream comprising hydrocarbon and hydrogen and a second stream comprising oxygen with separate surfaces of a membrane impervious to non-oxygen containing gases, wherein the membrane comprises a metal oxide selective for hydrogen combustion, and recovering selective hydrogen combustion product. The metal oxide is typically a mixed metal oxide of bismuth, indium, antimony, thallium and/or zinc.

U.S. Pat. No. 5,527,979, incorporated herein by reference, describes a process for the net catalytic oxidative dehydrogenation of alkanes to produce alkenes. The process involves simultaneous equilibrium dehydrogenation of alkanes to alkenes and the selective combustion of the hydrogen formed to drive the equilibrium dehydrogenation reaction further to the product alkenes. In particular, the alkane feed is dehydrogenated over an equilibrium dehydrogenation catalyst in a first reactor, and the effluent from the first reactor, along with oxygen, is then passed into a second reactor containing a metal oxide catalyst which serves to selectively catalyze the combustion of hydrogen. The equilibrium dehydrogenation catalyst may comprise platinum and the selective metal oxide combustion catalyst may contain bismuth, antimony, indium, zinc, thallium, lead and tellurium or a mixture thereof.

U.S. Patent Application Publication No. 2004/0152586, published Aug. 5, 2004 and incorporated herein by reference, describes a process for reducing the hydrogen content of the effluent from a cracking reactor. The process employs a catalyst system comprising (1) at least one solid acid cracking component and (2) at least one metal-based selective hydrogen combustion component consisting essentially of (a) a metal combination selected from the group consisting of: i) at least one metal from Group 3 and at least one metal from Groups 4-15 of the Periodic Table of the Elements; ii) at least one metal from Groups 5-15 of the Periodic Table of the Elements, and at least one metal from at least one of Groups 1, 2, and 4 of the Periodic Table of the Elements; iii) at least one metal from Groups 1-2, at least one metal from Group 3, and at least one metal from Groups 4-15 of the Periodic Table of the Elements; and iv) two or more metals from Groups 4-15 of the Periodic Table of the Elements; and (b) at least one of oxygen and sulfur, wherein the at least one of oxygen and sulfur is chemically bound both within and between the metals.

The selective hydrogen combustion reaction of the present invention is generally conducted at a temperature in the range of from about 300° C. to about 850° C. and a pressure in the range of from about 1 atm to about 20 atm (100 to 2000 kPa).

Aromatic Product Recovery/Treatment

In addition to hydrogen, the other major products of the dehydrocyclization step are benzene and naphthalene. These products can be separated from the dehydrocyclization effluent, typically by solvent extraction followed by fractionation, and then sold directly as commodity chemicals. Alternatively, some or all of the benzene and/or naphthalene can be alkylated to produce, for example, toluene, xylenes and alkyl naphthalenes and/or can be subjected to hydrogenation to produce, for example, cyclohexane, cyclohexene, dihydronaphthalene (benzylcyclohexene), tetrahydronaphthalene (tetralin), hexahydronaphthalene (dicyclohexene), octahydronaphthalene and/or decahydronaphthalene (decalin). Suitable alkylation and hydrogenation processes are described below and in more detail in our copending PCT Application Serial Nos. PCT/US2005/043523, filed on Dec. 2, 2005 and PCT/US2005/044038, filed on Dec. 2, 2005.

Aromatics Alkylation

Alkylation of aromatic compounds such as benzene and naphthalene is well known in the art and typically involves reaction of an olefin, alcohol or alkyl halide with the aromatic species in the gas or liquid phase in the presence of an acid catalyst. Suitable acid catalysts include medium pore zeolites (i.e., those having a Constraint Index of 2-12 as defined in U.S. Pat. No. 4,016,218), including materials having the framework types MFI (e.g., ZSM-5 and silicalite), MEL (e.g., ZSM-11), MTW (e.g., ZSM-12), TON (e.g., ZSM-22), MTT (e.g., ZSM-23), MFS (e.g., ZSM-57) and FER (e.g., ZSM-35) and ZSM-48, as well as large pore zeolites (i.e., those having a Constraint Index of less than 2) such as materials having the framework types BEA (e.g., zeolite beta), FAU (e.g., ZSM-3, ZSM-20, zeolites X, Y, ultrastabilized Y and dealuminized Y), MOR (e.g., mordenite), MAZ (e.g., ZSM-4), MEI (e.g., ZSM-18) and MWW (e.g., MCM-22, PSH-3, SSZ-25, ERB-1, ITQ-1, ITQ-2, MCM-36, MCM-49 and MCM-56).

In one embodiment of the present process, benzene is recovered from the dehydrocyclization effluent and then alkylated with an olefin, such as ethylene produced as a by-product of a hydrogen rejection step employing ethanation/methanation. Typical conditions for carrying out the vapor phase alkylation of benzene with ethylene include a temperature of from about 650 to 900° F. (343 to 482° C.), a pressure of about atmospheric to about 3000 psig (100 to 20,800 kPa), a WHSV based on ethylene of from about 0.5 to about 2.0 $hr^{-1}$ and a mole ratio of benzene to ethylene of from 1:1 to 30:1. Liquid phase alkylation of benzene with ethylene may be carried out at a temperature between 300 and 650° F. (150 to 340° C.), a pressure up to about 3000 psig (20,800 kPa), a WHSV based on ethylene of from about 0.1 to about 20 $hr^{-1}$ and a mole ratio of benzene to ethylene of from 1:1 to 30:1.

Conveniently, the benzene ethylation is conducted under at least partial liquid phase conditions using a catalyst comprising at least one of zeolite beta, zeolite Y, MCM-22, PSH-3, SSZ-25, ERB-1, ITQ-1, ITQ-2, ITQ-13, ZSM-5 MCM-36, MCM-49 and MCM-56.

The benzene ethylation can be conducted at the site of the dehydrocyclization/hydrogen rejection process or the benzene can be shipped to another location for conversion to ethylbenzene. The resultant ethylbenzene can then be sold, used as a precursor in, for example, the production of styrene or isomerized by methods well known in the art to mixed xylenes.

In another embodiment of the present process, the alkylating agent is methanol or dimethylether (DME) and is used to alkylate benzene and/or naphthalene recovered from the dehydrocyclization effluent to produce toluene, xylenes, methylnaphthalenes and/or dimethylnaphthalenes. Where the methanol or DME is used to alkylate benzene, this is conveniently effected in presence of catalyst comprising a zeolite, such as ZSM-5, zeolite beta, ITQ-13, MCM-22, MCM-49, ZSM-11, ZSM-12, ZSM-22, ZSM-23, ZSM-35, and ZSM-48, which has been modified by steaming so as to have a Diffusion Parameter for 2,2 dimethylbutane of about 0.1-15 $sec^{-1}$ when measured at a temperature of 120° C. and a 2,2 dimethylbutane pressure of 60 torr (8 kPa). Such a process is selective to the production of para-xylene and is described in, for example, U.S. Pat. No. 6,504,272, incorporated herein by reference. Where the methanol is used to alkylate naphthalene, this is conveniently effected in the presence of a catalyst comprising ZSM-5, MCM-22, PSH-3, SSZ-25, ERB-1, ITQ-1, ITQ-2, ITQ-13, MCM-36, MCM-49 or MCM-56. Such a process can be used to selectively produce 2,6-dimethylnaphthalene and is described in, for example, U.S. Pat. Nos. 4,795,847 and 5,001,295, incorporated herein by reference.

Where methanol or DME is used as an alkylating agent in the process of the invention, it can be provided as a separate feed to the process or can at least partly be generated in situ by adding a carbon dioxide-containing feed gas, such as a natural gas stream, to part or all of the effluent from the dehydrocyclization step. In particular, the dehydrocyclization effluent, prior to any separation of the aromatic components, can be fed to a reverse shift reactor and reacted with the carbon dioxide-containing feed under conditions to increase the carbon monoxide content of the effluent by reactions, such as Reactions 5 and 8 above.

In addition, methane and $CO_2$ and/or steam may be fed to a reverse shift reactor to generate syngas which can then be mixed with a portion of the dehydrocyclization effluent to adjust the $H_2/CO/CO_2$ ratios as required for the alkylation step.

Typically, the reverse shift reactor contains a catalyst comprising a transition metal on a support, such as Fe, Ni, Cr, Zn on alumina, silica or titania, and is operated under conditions including a temperature of about 500° C. to about 1200° C., such as about 600° C. to about 1000° C., for example about 700° C. to about 950° C. and a pressure of about 1 kPa to about 10,000 kPa, such as about 2,000 kPa to about 10,000 kPa, for example about 3000 kPa to about 5,000 kPa. Gas hourly space velocities may vary depending upon the type of process used, but generally the gas hourly space velocity of flow of gas through the catalyst bed is in the range of about 50 $hr^{-1}$ to about 50,000 $hr^{-1}$, such as about 250 $hr^{-1}$ to about 25,000 $hr^{-1}$, more for example about 500 $hr^{-1}$ to about 10,000 $hr^{-1}$.

The effluent from the reverse shift reactor can then be fed to an alkylation reactor operating under conditions to cause reactions such as the following to occur:

$$CO + 2H_2 \leftrightarrow CH_3OH \quad \text{(Reaction 9)}$$

$$CH_3OH + C_6H_6 \rightarrow toluene + H_2O \quad \text{(Reaction 10)}$$

$$2CH_3OH + C_6H_6 \rightarrow xylenes + 2H_2O \quad \text{(Reaction 11)}$$

Suitable conditions for such an alkylation reactor would include a temperature of about 100 to about 700° C., a pressure of about 1 to about 300 atmospheres (100 to 30,000 kPa), and a WHSV for the aromatic hydrocarbon of about 0.01 to about 100 $hr^{-1}$. A suitable catalyst would comprise a molecular sieve having a constraint index of 1 to 12, such as ZSM-5, typically together with one or metals or metal oxides, such as copper, chromium and/or zinc oxide.

Conveniently, where the alkylation catalyst includes a molecular sieve, the latter is modified to change its diffusion characteristics such that the predominant xylene isomer produced by Reaction 11 is paraxylene. Suitable means of diffusion modification include steaming and ex-situ or in-situ deposition of silicon compounds, coke, metal oxides, such as MgO, and/or P on the surface or in the pore mouths of the molecular sieve. Also preferred is that an active metal be incorporated into the molecular sieve so as to saturate more highly reactive species, such as olefins, which may be generated as by-products and which could otherwise cause catalyst deactivation.

The effluent from the alkylation reactor could then be fed to a separation section in which the aromatic products would initially be separated from the hydrogen and other low molecular weight materials, conveniently by solvent extraction. The aromatics products could then be fractionated into a benzene fraction, a toluene fraction, a $C_8$ fraction and a heavy fraction containing naphthalene and alkylated naphthalenes. The $C_8$ aromatic fraction could then be fed to a crystallization or sorption process to separate the valuable p-xylene component and the remaining mixed xylenes either sold as product or fed to an isomerization loop to generate more p-xylene. The toluene fraction could either be removed as saleable product, recycled to the alkylation reactor or fed to a toluene disproportionation unit, such as a selective toluene disproportionation unit for the preparation of additional p-xylene.

Aromatics Hydrogenation

In addition to or instead of the alkylation step, at least part of the aromatic components in the dehydrocyclization effluent can be hydrogenated to generate useful products such as cyclohexane, cyclohexene, dihydronaphthalene (benzylcyclohexene), tetrahydronaphthalene (tetralin), hexahydronaphthalene (dicyclohexene), octahydronaphthalene and/or decahydronaphthalene (decalin). These products can be employed as fuels and chemical intermediates and, in the case of tetralin and decalin, can be used as the solvent for extracting the aromatic components from the dehydrocyclization effluent.

The hydrogenation is conveniently, but not necessarily, conducted after separation of the aromatic components from the dehydrocyclization effluent and conveniently employs part of the hydrogen generated by the dehydrocyclization reaction. Suitable aromatic hydrogenation processes are well known in the art and typically employ a catalyst comprising Ni, Pd, Pt, Ni/Mo or sulfided Ni/Mo supported on alumina or silica support. Suitable operating conditions for the hydrogenation process include a temperature of about 300 to about 1,000° F. (150 to 540° C.), such as about 500 to about 700° F. (260 to 370° C.), a pressure of about 50 to about 2,000 psig (445 to 13890 kPa), such as about 100 to about 500 psig (790 to 3550 kPa) and a WHSV of about 0.5 to about 50 $hr^{-1}$, such as about 2 to about 10 $hr^{-1}$.

Partial hydrogenation to leave one or more olefinic carbon-carbon bonds in the product may also be desirable so as to produce materials suitable for polymerization or other downstream chemical conversion. Suitable partial hydrogenation processes are well known in the art and typically employ a catalyst comprising noble metals with ruthenium being preferred supported on metallic oxides, such as $La_2O_3$—ZnO. Homogeneous noble metal catalyst systems can also be used. Examples of partial hydrogenation processes are disclosed in U.S. Pat. Nos. 4,678,861; 4,734,536; 5,457,251; 5,656,761; 5,969,202; and 5,973,218, the entire contents of which are incorporated herein by reference.

An alternative hydrogenation process involves low pressure hydrocracking of the naphthalene component to produce alkylbenzenes over a catalyst such as sulfided Ni/W or sulfided Ni supported on an amorphous aluminosilicate or a zeolite, such as zeolite X, zeolite Y or zeolite beta. Suitable operating conditions for low pressure hydrocracking include a temperature of about 300 to about 1,000° F. (150 to 540° C.), such as about 500 to about 700° F. (260 to 370° C.), a pressure of about 50 to about 2,000 psig (445 to 13890 kPa), such as about 100 to about 500 psig (790 to 3550 kPa) and a WHSV of about 0.5 to about 50 hr$^{-1}$, such as about 2 to about 10 hr$^{-1}$.

The invention will now be more particularly described with reference to the accompanying drawings and the following non-limiting Examples.

Referring to FIG. 1, the drawing illustrates a simplified design of a dehydrocyclization reactor system for converting methane to aromatics according to one embodiment of this disclosure. In this embodiment, the dehydrocyclization reactor includes a settling bed reaction zone, 11, in which catalytic particulate material is moved from top of the reaction zone to the bottom of the reaction zone, while the feed is passed through the reaction zone in the opposite direction. The heated catalytic particulate material flows through an inlet located adjacent the top of the reactor 11 via line 12. The cooled catalytic particulate material flows out of the reactor 11 via outlets located adjacent the base of the reactor 11 and withdrawn via lines 13 and 14. Methane feed is introduced into the reactor 11 adjacent the base thereof via line 15. The product and unreacted methane flows out of reactor 11 via outlet 16 adjacent to the top of reactor 11. Typically, the heated catalyst enters the reactor 11 at a temperature of about 850° C. and the cooled catalyst leaves the reactor at a temperature of about 600° C. FIG. 1 portrays the reactor 11 being one reaction zone. However one having ordinary skill in the art understands that the reactor system may contain more than one zone.

Figure 2:
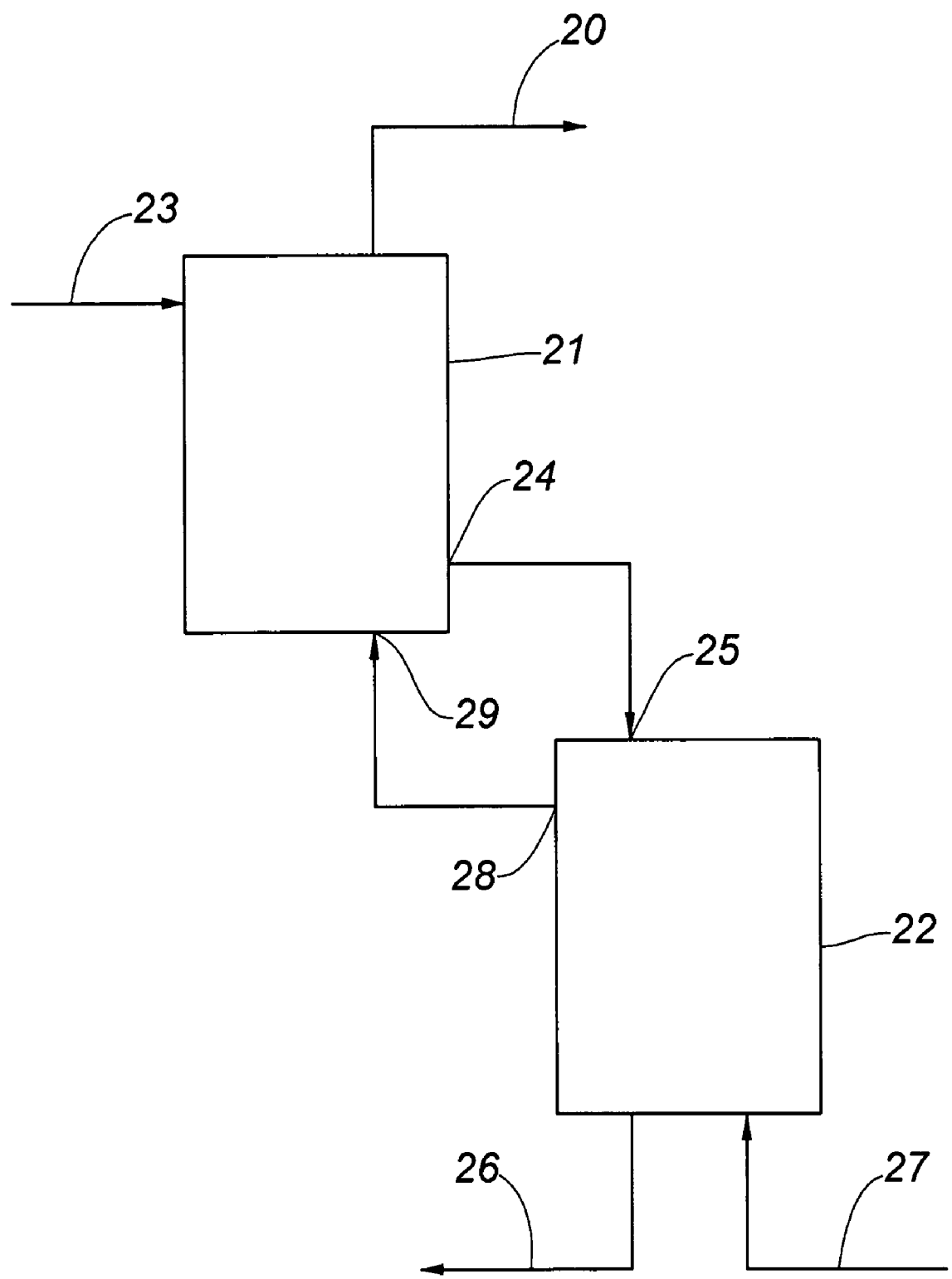
FIG. 2 is a diagram of a process for converting methane to higher hydrocarbons according to a second embodiment of the invention.

Referring to FIG. 2, the drawing illustrates a simplified design of a dehydrocyclization reactor system for converting methane to aromatics according to one embodiment of the invention. In this embodiment, the dehydrocyclization reactor includes two series-connected moving bed reactors, 21 and 22, in which particulate catalyst is cascaded in one direction from one reactor to the next adjacent reactor in the series, while the feed is passed through and between the reactors in the opposite direction. The heated catalyst flows through an inlet located adjacent the top of the reactor 21 via line 23 and from which cooled catalyst flows via outlet 24 located adjacent the base of the reactor 21 into the reactor 22 via inlet 25. The catalyst flows out of reactor 22 via an outlet adjacent the base of the reactor 22 via line 26. Methane feed 27 is introduced into the reactor 22 adjacent the base thereof via line 27. The product and unreacted methane flows out of reactor 22 through an outlet adjacent to the top of reactor 22 via outlet 29 and feeds to reactor 21 via an inlet adjacent to the base of thereof via line 28. The final product is removed from reactor 21 through an outlet adjacent to the top of the reactor 21 via line 20. Typically, the heated catalyst enters the reactor 21 at a temperature of about 850° C. and the cooled catalyst leaves the reactor 22 at a temperature of about 600° C. FIG. 2 portrays the zones being in separate vessels however the two zones may be located in a single vessel with appropriate internals to maintain the two zones. One having ordinary skill in the art understands that the reactor system may contain more than two cascade moving beds, e.g., 3, 4, or 5 series-connected moving beds reactors or zones.

One having ordinary skill in the art understands that the embodiments discussed in this application do not represent all the possible apparatus or process variations embodied by the present disclosure. In addition, many pieces of equipment and apparatus and certain processing steps may be needed for industrial, commercial or even experimental purposes. Examples of such equipments and apparatus and processing steps are, but not limited to, distillation columns, fractionation columns, heat exchanges, pumps, valves, pressure gauges, temperature gauges, liquid-vapor separators, feed and product driers and/or treaters, clay treaters, feed and/or product storage facilities, and processes and steps for process control. While such equipment, apparatus and steps that are not needed for understanding the essence of the present disclosure are not shown in the drawings, some of them may be mentioned from time to time to illustrate various aspects of the invention. It is also noted that some of the equipment may be placed at different places in the process depending on the conditions of the processes.

The invention will now be more particularly described with reference to the following non-limiting Examples.

EXAMPLE 1

Example 1 demonstrates the use of co-feeds (such as $H_2$, $CO_2$ and $H_2O$) in order to achieve reduced coking rate of Mo/ZSM-5 catalyst during dehydrocyclization of methane to form primarily benzene. Example 2 will demonstrate that by reducing the amount of coke that is deposited on the catalyst during the on-oil period, it is possible to maintain high performance after multiple on-oil and regeneration cycles and that the lower single-cycle coking rate translates to a lower net coke deposition rate over multiple cycles.

Mo/ZSM-5 catalysts were prepared using two methods: (1) via impregnation of the required amount of ammonium heptamolybdate solution onto a $NH_4$+-ZSM-5 support (having a $Si/Al_2$ ratio of 25) via incipient wetness, followed by drying at 120° C. for 2 hours and final calcination at 500° C. for 6 hours in flowing air, and (2) ball-milling molybdenum oxide with $NH_4$+-ZSM-5 support (having a $Si/Al_2$ ratio of 25) for 2 hours, followed by calcination at 500° C. for 5 hours in flowing air. The molybdenum loading (wt % metal basis) was varied by changing the ammonium heptamolybdate concentration in the impregnating solution or the amount of molybdenum oxide added to milling mixture. Catalytic testing of the resultant Mo/ZSM-5 catalysts was performed using a Tapered-Element Oscillating Microbalance (TEOM), allowing accurate determination of catalyst mass changes during reaction with fast response times. The catalyst (after calcination) was pelletized, crushed and sieved to 20-40 mesh particle size. Approximately 0.10 grams of sieved catalyst particles were loaded into the TEOM sample holder (0.20 cc total sample volume), and packed to form a fixed-bed using quartz wool supports. Catalyst performance for methane dehydrocyclization to benzene was performed at 800° C. and 20 psia (138 kPa) for Runs A-B or 14.7 psia (101 kPa) for Runs C-E in Table 1 using a feed containing specified co-feeds ($CO_2$, $H_2O$, $H_2$), Ar (where Ar is used as internal standard) and balance $CH_4$ at a weight-hourly space velocity (based on methane) as specified. The reaction effluent was analyzed using a mass spectrometer to determine the methane, benzene, naphthalene, hydrogen and argon concentrations. The rate of coke deposition on the catalyst (i.e., heavy carbonaceous deposit which does not volatize from catalyst surface) was determined directly via mass changes observed using the microbalance. The reported values for catalyst performance (e.g., benzene productivity, methane converted, benzene selectivity) are cumulative or average values for the time period beginning at methane injection and ending when the instantaneous benzene yield declines to <2%. The results are shown in Table 1.

TABLE 1

| Run | wt % Mo | Co-feeds | Avg. Coking Rate (wt %/h) | Benzene Productivity (g Bz/g Cat) | Methane Converted (g $CH_4$/g Cat) | Wt % Benzene Selectivity |
|---|---|---|---|---|---|---|
| A | 4.6 | None | 5.2 | 0.50 | 0.93 | 54 |
| B | 4.6 | 2% $CO_2$, 10% $H_2$ | 2.2 | 1.31 | 2.21 | 59 |
| C | 2.7 | None | 8.6 | 0.23 | 0.61 | 38 |
| D | 2.7 | 3% $H_2O$ | 6.0 | 0.34 | 0.85 | 40 |
| E | 2.7 | 20% $H_2$ | 3.8 | 0.26 | 0.49 | 53 |

As shown in Table 1, at a Mo loading of 4.6% for Run A & B, the average coke deposition rate decreased from 5.2 wt % per hour for the case with no co-feeds (i.e., feed composition of 95% $CH_4$-5% Ar) to 2.2 wt % per hour for the case with 2% $CO_2$ and 10% $H_2$ co-feed (i.e., feed composition of 2% $CO_2$, 10% $H_2$, 83.6% $CH_4$ and 4.4% Ar). The benzene productivity increased from 0.5 g benzene formed per g of catalyst for no co-feed case to 1.3 g benzene per g catalyst. This demonstrates that the presence of $CO_2$ and $H_2$ co-feeds can significantly improve benzene productivity of Mo/ZSM-5 catalysts by decreasing coking rates. Run C, D and E demonstrate the effect of $H_2O$ and $H_2$ co-feeds on a catalyst comprising 2.7% Mo on ZSM-5. The average coking rate was found to decrease from 8.6 wt %/h without co-feed to 6.0 wt %/h with 3% steam co-feed, and to 3.8 wt %/h with 20% $H_2$ co-feed. In both cases, the benzene productivity and selectivity were found to increase with the addition of co-feed.

EXAMPLE 2

Mo/ZSM-5 catalysts were prepared using methods described earlier in Example 1. The as-synthesized catalysts were subjected to cyclic aging which consisted of (1) an on-oil period where the catalyst was exposed to $CH_4$ feed at 800° C. and 14.7 psia (101 kpa) with specified co-feeds for 5 min at specified WHSV based on $CH_4$ followed by (2) a regeneration period where the catalyst was heated to 850° C. and 14.7 psia (101 kPa) under $H_2$ gas at 10 C/min and held at 850° C. for a specified time at a GHSV of 9000 cc [STP]/g-catalyst/hr. After completion of the regeneration step, the catalyst was cooled to 800° C. before reinjection of methane feed. Prior to cyclic aging, the as-synthesized catalyst was pre-carburized by heating the catalyst in a 15% $CH_4$—$H_2$ gas mixture from 150° C. to 800° C. at 5 C/min and held at 800° C. for 1 hour. After the catalysts were subjected to a specified number of on-oil and regeneration cycles, the spent catalysts were removed and tested for performance in the TEOM.

Approximately 0.10 grams of the spent catalyst were loaded into the TEOM sample holder, and packed to form a fixed-bed using quartz wool supports. Catalyst performance for methane dehydrocyclization to benzene was performed at 800° C. and 14.7 psia (101 kPa) for Runs A-D and 20 psia (138 kPa) for Runs E-G in Table 2 using a 95% $CH_4$-5% Ar feed (where Ar is used as internal standard) and at a weight-hourly space velocity of 4 g $CH_4$ fed per g catalyst per hour. The reaction effluent was analyzed using a mass spectrometer to determine the methane, benzene, naphthalene, hydrogen and argon concentrations. Determination of coke on catalyst was performed using temperature-programmed oxidation of spent catalyst in a Thermal Gravimetric Analyzer (TGA).

Table 2 compares the accumulated coke on catalyst after multiple on-oil and regeneration cycles and the residual benzene productivity of the spent catalysts. Run A-C shows the performance of 2.7% Mo/ZSM-5 catalyst after 0, 20 and 40 cycles. Run D shows the performance of 2.7% Mo/ZSM-5 catalyst after 40 cycles. Run E-G shows the performance of 4.6% Mo/ZSM-5 catalyst after 0, 50 and 389 cycles. Comparing Run C and D, it will be seen that the addition of 20% $H_2$ co-feed reduced the net coke deposited on the catalyst by about 55% from 2.0 wt % (for the no co-feed case) to 0.9 wt % (for 20% $H_2$ co-feed). In addition to decreasing coke, the benzene productivity after 40 cycles was found to be significantly higher by about 25% with 20% $H_2$ co-feed (0.25 g benzene/g catalyst) versus no co-feed case (0.20 g benzene/g catalyst). Runs E-G demonstrate that the net accumulation of coke on catalyst can be further minimized via the addition of 2% $CO_2$ co-feed. After 50 cycles, the net coke on catalyst was found to be only 0.15 wt %, which is significantly lower (by about 93%) than the coke on catalyst observed after 40 cycles for the no co-feed case (i.e., 2.0 wt %), even though the feed WHSV during the on-oil period was increased from 1 to 4. After 50 cycles, no deterioration in benzene productivity was observed. After 389 cycles, the coke on catalyst was measured to be about 0.5 wt %, indicating that the net accumulation of coke on catalyst can be minimized over long-term cyclic aging.

TABLE 2

| Run | % Mo | # of Cycles | Co-Feeds | On-Oil Conditions | Regen Conditions | Coke on Aged Catalyst (wt %) | % Change in wt % Coke | Benzene Productivity (g CH4/g Cat) | % Change in Benzene Productivity |
|---|---|---|---|---|---|---|---|---|---|
| A | 2.7 | 0 | n/a | n/a | n/a | 0.0 | | 0.21 | Basis for B–D |
| B | 2.7 | 20 | None | 5 min, 1 WHSV | 40 min; 850 C | 1.6 | | 0.28 | 33 |
| C | 2.7 | 40 | None | 5 min, 1 WHSV | 40 min; 850 C | 2.0 | Basis | 0.20 | −5 |
| D | 2.7 | 40 | 20% H2 | 5 min, 1 WHSV | 40 min; 850 C | 0.9 | −55 | 0.25 | 19 |
| E | 4.6 | 0 | n/a | n/a | n/a | 0.00 | | 0.50 | Basis for F |
| F | 4.6 | 50 | 2% CO2, 25% H2 | 5 min, 4 WHSV | 5 min; 850 C | 0.15 | −93 | 0.59 | 18 |
| G | 4.6 | 389 | 2% CO2, 25% H2 | 5 min, 4 WHSV | 5 min; 850 C | 0.50 | −75 | tbd | tbd |

EXAMPLE 3

This example is intended to show that higher pressure regeneration has the benefit of improving the catalyst selectivity; that is, by increasing the selectivity to benzene and reducing the selectivity to coke production.

A catalyst comprising about 4 wt % Mo on ZSM-5 was used to aromatize a feed comprising $CH_4$ 86.65 mol %, $C_2H_6$ 1.8%, $CO_2$ 0.9%, $H_2$ 0.45% and Ar 10 mol %. The effluent was monitored by gas chromatography to calculate benzene yields. The catalyst was run with alternating reaction and regeneration cycles, with the methane-containing feed being supplied to the catalyst during each 20 minute reaction cycle, and hydrogen being supplied to the catalyst during each 40 minute regeneration cycle. For the first 90% of each reaction cycle, a 20% $H_2$ co-feed was added to the methane-containing feed but terminated during the final 10% of each reaction cycle. The reaction pressure was about 7 psig (149 kPa), whereas the reaction temperature was increased during each reaction cycle from an initial value of about 700° C. to a final value of about 800° C. The average temperature during each regeneration cycle was about 850° C., with the maximum temperature being 860° C. At the start of the test run, the pressure during each regeneration cycle was 34 psig (335 kPa), and the stabilized selectivities and benzene yields are listed below. After a predetermined time, the pressure during each regeneration cycle was reduced to about 7 psig. (149 kPa) and, about 11 hours after the change in regeneration pressure, the selectivities and benzene yields were again measured and are reported below. It will be seen that the benzene selectivity and yield are higher, and coke selectivity is lower, at the higher regeneration pressure.

|  | 34 psig | 7 psig |
|---|---|---|
| Benzene yield, % feed carbon | 10.7 | 8.9 |
| Selectivities, % feed carbon converted: |  |  |
| Benzene | 65.0 | 57.1 |
| Coke | 13.1 | 19.5 |

EXAMPLE 4

Mo/ZSM-5 catalysts were prepared via impregnation of required amount of ammonium heptamolybdate solution onto $NH_4ZSM$-5 support (having a $Si/Al_2$ ratio of 28) via incipient wetness, followed by drying at 120° C. for 2 hours and final calcination at 500° C. for 6 hours in flowing air. A nominal molybdenum loading (wt. % of metal based on the total weight of the catalyst) was targeted of 2.7 wt. %; minor variations in molybdenum loadings do not affect the conclusions obtained. Each Mo/ZSM-5 catalyst sample (after calcination) was pelletized, crushed and sieved to 30-60 mesh particle size. Catalytic testing of the Mo/ZSM-5 catalysts was performed in a quartz reactor packed to form a fixed-bed using quartz wool supports.

Catalyst performance for methane dehydrocyclization to benzene was performed at various temperatures using a 95 wt. % $CH_4$-5 wt. % argon feed (argon is used as internal standard) at a weight-hourly space velocity (based on methane) of 1.2 $hr^{-1}$. All experimental data was obtained at 138 kPa-a (20 psia) and all modeling was also performed at the same pressure. The reaction effluent was analyzed using a mass spectrometer and gas chromatograph to determine the methane, benzene, toluene, ethylene, naphthalene, hydrogen, and argon concentrations. The rate of coke deposition on the catalyst (i.e., heavy carbonaceous deposit which does not volatize from catalyst surface) was determined via carbon balance. Additional data was obtained at two temperatures (750° C. and 800° C.) with $H_2$ added to the feed at 6 mol % and 20 mol % respectively.

For the purposes of Example 4 the experimental data were consolidated to two values $Sel_{BTN}$ and $Sel_{Coke}$. The $Sel_{BTN}$ is the average selectivity on a carbon molar basis as defined by the sum of the moles of carbon in the product present in benzene, toluene, and naphthalene divided by the moles of carbon contained in methane that reacted. The $Sel_{Coke}$ is the average selectivity on a carbon molar basis as defined by the sum of the moles of carbon that remains in the reactor divided by the moles of carbon contained in methane that reacted. The sum of $Sel_{BTN}$ and $Sel_{Coke}$ does not equal to 100% due to the formation of other minor products, predominately ethylene. As it is often difficult to obtain accurate experimental thermodynamic conversion data, commercially available simulation software (PROII/6.0 Copyright 2003 Invensys Systems Inc.) was utilized to establish the value $Conv_{BL}$. The $Conv_{BL}$ is defined as the maximum thermodynamically obtainable conversion of methane to benzene and hydrogen (i.e., no model constrained so that no other products such as coke, naphthalene, ethylene, etc) at a given temperature and 138 kpa-a (20 psia) pressure. The experimental and modeling results are shown in Table 3.

TABLE 3

| Temp ° C. | $H_2$ Co-Feed Mol % | $Sel_{BTN}$ | $Sel_{Coke}$ % C on Feed | $Conv_{BL}$ |
|---|---|---|---|---|
| 600 | 0% | 99% | 0.01% | 5% |
| 650 | 0% | 98% | 0.1% | 8% |
| 700 | 0% | 96% | 1% | 12% |
| 750 | 0% | 85% | 9% | 17% |
| 750 | 6% | 89% | 5% |  |
| 800 | 0% | 68% | 24% | 23% |
| 800 | 20% | 84% | 8% |  |
| 850 | 0% | 45% | 46% | 29% |
| 900 | 0% | 20% | 71% | 37% |

It is understood that different catalyst compositions, the use of co-feeds ($CO_2$, CO, $H_2O$, $H_2$, $O_2$, ethane, propane, etc), different operating pressures, and/or different space velocities may change the selectivity and conversion numbers but that, while the exact level of improvement demonstrated by this disclosure may change, the directional improvements obtained by this disclosure will still be achieved. In addition, it is to be appreciated that, as a basis for the modeling calculations discussed below, it is assumed that the methane feed to the reactor was always preheated to the same temperature (600° C.) and in all cases a nominal feed rate of methane of 100 kilograms per hour was used. It was also used as a basis that the catalyst supplied to the moving bed reactor systems was maintained at the same temperature (850° C.). The quantity of catalyst required to maintain this temperature was calculated for each reactor configuration. For simplicity, it is assumed that the catalyst thermal conductivity, thermal diffusivity and surface emissivity remain constant. The following Table 4 lists the physical constants and catalyst properties used in the calculations.

TABLE 4

| Model Parameters | |
| --- | --- |
| Catalyst Particle Density | 1400 kg/m³ |
| Catalyst Heat Capacity | 1262 J/kg-K |
| Catalyst Thermal Conductivity | 0.4 W/m-K |
| Catalyst Thermal Diffusivity | 2.26 × 10⁻⁷ m²/s |
| Catalyst Surface Emissivity | 0.85 |

To allow modeling of various reactor configurations, equations were obtained for $Sel_{BTN}$, $Sel_{Coke}$, and $Conv_{BL}$ by obtaining best fit polynomial equations for the above set of data points; the data points where $H_2$ was included in the feed were not included in the calculations of the equations. The equations obtained and the $R^2$ values are shown below:

$Sel_{BTN} = (1.81818181818345E-10)T^4 - (5.41010101010501E-07)T^3 + (5.88000000000377E-04)T^2 - (2.78591414141575E-01)T + 4.97583333333585E+01$ $R^2_{BTN} = 9.99810335105254E-01$ $Sel_{Coke} = (-1.85878787878687E-10)T^4 + (5.62280808080511E-07)T^3 - (6.21721666666349E-04)T^2 + (2.99664027416883E-01)T - 5.33408809523590E+01$ $R^2_{Coke} = 9.99958406639717E-01$ $Conv_{BL} = (1.91428571428569E-06)T^2 - (1.81714285714283E-03)T + 4.53357142857135E-01$ $R^2_{BL} = 9.99955208049633E-01$ where T is temperature in degrees C., In all examples $R^2$ is the coefficient of determination which compares estimated and actual y-values, and ranges in value from 0 to 1. If it is 1, there is a perfect correlation in the sample—there is no difference between the estimated y-value and the actual y-value. At the other extreme, if the coefficient of determination is 0, the regression equation is not helpful in predicting a y-value. The version used here is based on an analysis of variance decomposition as follows:

$$R^2 = \frac{SS_R}{SS_T} = 1 - \frac{SS_E}{SS_T}.$$

In the above definition, $$SS_T = \sum_i (y_i - \bar{y})^2, \ SS_R = \sum_i (\hat{y}_i - \bar{y})^2, \ SS_E = \sum_i (y_i - \hat{y}_i)^2.$$

That is, $SS_T$ is the total sum of squares, $SS_R$ is the regression sum of squares, and $SS_E$ is the sum of squared errors.

$R^2_{BTN}$ is coefficient of determination for the $Sel_{BTN}$ correlation, $R^2_{Coke}$ is coefficient of determination for the $Sel_{Coke}$ correlation, and $R^2_{BL}$ is coefficient of determination for the $Conv_{BL}$ correlation.

These set of equations was used to calculate the yields that would be obtained for various reactor configurations where $Yield_{BTN}$ was defined as $Sel_{BTN} \times Conv_{BL}$ integrated over the temperature profile in the reactor system and $Yield_{Coke}$ was defined as $Sel_{Coke} \times Conv_{BL}$ integrated over the temperature profile in the reactor system. While it is recognized and shown in the Table 3, that the byproduct $H_2$ improved the reaction selectivity, these equations omitted the selectivity improvement so that they provided a conservative estimate as to the level of improvement that the present process would provide.

Transport or Riser Reactor—Comparative

Utilizing the above equations for a transport or riser reactor with adiabatic declining temperature with an inlet temperature of 850° C. the required catalyst circulation rate to maintain an outlet temperature of 800° C. was 3211 kilograms per hour (kg/hr) based on the nominal feed rate of methane of 100 kg/hr at 600° C. The following yields and selectivities were calculated:

$Sel_{BTN} = 51\%$
$Sel_{Coke} = 40\%$
$Yield_{BTN} = 12\%$
$Yield_{Coke} = 8.9\%$
$\Delta T_{Reaction} = -50°$ C. (negative 50° C.);

wherein $\Delta T_{Reaction}$ is defined as the product outlet reaction temperature (i.e., the last temperature at which catalytic reaction occurs before the hydrocarbon product leaves the reactor system) minus the hydrocarbon feed inlet reaction temperature (i.e., the first temperature at which catalytic reaction occurs when the hydrocarbon feed enters the reactor system).

Adiabatic Fixed Bed Reactor—Comparative

Performing modeling of the potential fixed bed comparatives resulted in even poorer performance than with the transport or riser reactor because in the fixed bed configuration the entire heat of reaction had to be supplied by the methane containing stream (since no moving catalyst was used to supply heat to the reaction zone). Therefore the fixed bed reactor required that the methane containing stream had to be heated to a temperature much greater than the desired outlet temperature of 800° C., thereby resulting in a larger magnitude $\Delta T_{Reaction}$; that is a $\Delta T_{Reaction}$ of −60° C. or more negative.

Settling Bed Reactor

In the case simulated for a settling bed of catalyst with an inverse temperature profile and a 50° C. approach temperature between the supplied catalyst and the process outlet temperature, the inlet was operated at 620° C. and the outlet was operated at 800° C., the catalyst circulation rate was reduced to 717 kg/hr and the reaction results were improved:

$Sel_{BTN} = 89\%$
$Sel_{Coke} = 7\%$
$Yield_{BTN} = 20\%$
$Yield_{Coke} = 1.5\%$
$\Delta T_{Reaction} = +180°$ C.

Cascaded Fluid Beds (2 Fluidized Beds)

Similar to what is shown in FIG. 2; this Example is for 2 cascaded fluid beds. By cascaded fluid beds it is meant that there are 2 or more reaction stages or zones operating at different temperatures with particulate catalyst moving from one stage to the next and hydrocarbon gas moving from one stage to the next in the direction opposite that of the catalyst movement. In the case simulated for two cascaded fluidized beds of catalyst, the first bed was operated at 731° C. and the second bed was operated at 800° C.; the required catalyst circulation rate was reduced to 1367 kg/hr and the reaction results were improved:

$Sel_{BTN}$=81%
$Sel_{Coke}$=13%
$Yield_{BTN}$=18%
$Yield_{Coke}$=2.8%
$\Delta T_{Reaction}$=+69° C.
$\Delta T_{Catalyst}$=−119° C. (negative 119° C.).

Cascaded Fluid Beds (3 Fluidized Beds)

In the case simulated for three cascaded fluidized beds of catalyst, the first bed was operated at 690° C., the second bed was operated at 753° C. and the third bed was operated at 800° C., the catalyst circulation rate was reduced to 1020 kg/hr and the reaction results were improved:

$Sel_{BTN}$=85%
$Sel_{Coke}$=10%
$Yield_{BTN}$=19%
$Yield_{Coke}$=2.2%
$\Delta T_{Reaction}$=+110° C.
$\Delta T_{Catalyst}$=−160° C. (negative 160° C.).

Cascaded Fluid Beds (4 Fluidized Beds)

In the case simulated for four cascaded fluidized beds of catalyst, the first bed was operated at 669° C., the second bed was operated at 723° C., the third bed was operated at 762° C., and the fourth bed was operated at 800° C., the catalyst circulation rate was reduced to 900 kg/hr and the reaction results were improved:

$Sel_{BTN}$=86%
$Sel_{Coke}$=9%
$Yield_{BTN}$=19%
$Yield_{Coke}$=2.0%
$\Delta T_{Reaction}$=+131° C.
$\Delta T_{catalyst}$=−181° C. (negative 181° C.).

Cascaded Fluid Beds (5 Fluidized Beds)

In the case simulated for five cascaded fluidized beds of catalyst, the first bed was operated at 655° C., the second bed was operate at 703° C., the third bed was operated at 737° C., the fourth bed was operated at 767° C., and the fifth bed was operated at 800° C., the catalyst circulation rate was reduced to 838 kg/hr and the reaction results were improved:

$Sel_{BTN}$=87%
$Sel_{Coke}$=8%
$Yield_{BTN}$=20%
$Yield_{Coke}$=1.8%
$\Delta T$=+145° C.
$\Delta T_{Catalyst}$=−195° C. (negative 195° C.).

As illustrated by the above cascaded fluid bed examples, more reaction zones achieve better results, although it will be appreciated that the reaction system investment will increase with increasing number of zones (or stages). There is optimum number of zones (or stages) which depends on the economic of the process.

Isothermal Fixed Bed—Comparative

In the case simulated for a single fixed beds of catalyst, the bed was operated at 800° C., and the results were:

$Sel_{BTN}$=68%
$Sel_{Coke}$=24%
$Yield_{BTN}$=15%
$Yield_{Coke}$=5.4%
$\Delta T_{Reaction}$=0° C.
$\Delta T_{Catalyst}$=Not applicable; fixed beds of catalyst Temperature Staged Isothermal Fixed Beds (2 Beds)

In the case simulated for two temperature staged fixed beds of catalyst, the first bed was operated at 700° C., the second bed was operated at 800° C., and the reaction results were improved:

$Sel_{BTN}$=83%
$Sel_{Coke}$=12%
$Yield_{BTN}$=19%
$Yield_{Coke}$=2.7%
$\Delta T_{Reaction}$=+100° C.
$\Delta T_{Catalyst}$=Not applicable; fixed beds of catalyst Temperature Staged Isothermal Fixed Beds (4 Beds)

In the case simulated for four temperature staged fixed beds of catalyst, the first bed was operated at 650° C., the second bed was operated at 700° C., the third bed was operated at 750° C., and the fourth bed was operated at 800° C., and the reaction results were improved:

$Sel_{BTN}$=87%
$Sel_{Coke}$=8%
$Yield_{BTN}$=20%
$Yield_{Coke}$=1.9%
$\Delta T_{Reaction}$=+150° C.
$\Delta T_{Catalyst}$=Not applicable; fixed beds of catalyst

EXAMPLE 5

Based on the model predicted advantages for an inverse temperature profile, a laboratory scale unit was constructed to validate the model results. While the model was oriented toward operation of the reaction system as a settling bed, the laboratory reactor was a fixed bed of catalyst with an inverse temperature profile imposed by use of external heaters. In all cases the experimentally observed conversions fell below the model predicted conversions. This may be due to laboratory scale experimental artifacts such as bed bypassing and or/back mixing due to the hydrodynamic regime in which the lab scale reactors operate.

Mo/ZSM-5 catalyst was prepared via ball milling of 7.5 wt % Mo (wt % of metal based on the total weight of the catalyst) as $MoO_3$ with $NH_4ZSM-5$ support (having a $Si/Al_2$ ratio of 25) for 2 hr, followed by calcination at 500° C. for 5 hr in air. The catalyst was pelletized, crushed, and sieved to 20-40 mesh particle size. Catalytic testing of the Mo/ZSM-5 catalyst was performed in a fixed bed quartz reactor with an inner diameter of 7 mm and a bed length of about 18 cm. Inert quartz particles (20-50 mesh) were used as a bed diluent so that all beds were the same length.

Catalyst performance for methane dehydrocyclization to benzene was performed using a 95 vol % $CH_4$/5 vol % Ar feed (argon was used as an internal standard). All experimental reaction data was obtained at 20 psia (138 kPa-a). The reaction effluent was analyzed using a mass spectrometer to determine product concentrations.

Ten separate catalyst performance experiments were conducted for comparison. In all experiments the catalyst was activated by heating in 15 vol % $CH_4$/80 vol % $H_2$/5 vol % Ar at 5° C./min to 800° C. and holding for 30 min. This was followed by aging the catalyst with 5 cycles of reaction and regeneration (also identical for all ten experiments). Each reaction segment lasted 20 minutes at 800° C. in 95 vol % $CH_4$/5 vol % Ar feed at 1.4 $hr^{-1}$ weight-hourly space velocity (WHSV) based on $CH_4$. Each regeneration segment consisted of switching to $H_2$, heating to 850° C. with a 10 min. hold time, then cooling back to 800° C. (total time on $H_2$ of 14 min.). The ten experiments differed only on their sixth reaction cycle which was run in 95 vol % $CH_4$/5 vol % Ar feed for 4 hours. Conditions for the sixth cycle were selected to compare the effects of catalyst bed temperature profile at different space velocities. In particular, experiments 1 to 5 were run at WHSV values varying between 0.25 and 8 hr$^{-1}$ with bed being held at isothermal conditions at 800° C. In contrast, experiments 6 to 10 were run over the same range of WHSV values but with a linear gradient in bed temperature of 650° C. at the feed inlet to 800° C. at the product outlet (inverse temperature profile). Table 5 summarizes the catalyst performance results for the ten experiments during reaction cycle #6.

TABLE 5

| Exp. # | WHSV (hr$^{-1}$) for cycle 6 | Methane conversion (%) at 1 hr | Benzene yield (%) at 1 hr | Benzene selectivity (%) at 1 hr | Methane conversion (%) at 4 hr | Benzene yield (%) at 4 hr | Benzene selectivity (%) at 4 hr | Total Benzene Produced (g C$_6$H$_6$/g Catalyst) | Increase in Total Benzene Produced |
|---|---|---|---|---|---|---|---|---|---|
| 1 | 0.25 | 17.4 | 10.3 | 60 | 12.5 | 4.5 | 36 | 0.06 | Base |
| 2 | 0.5 | 17.9 | 12.1 | 68 | 5.6 | 0.6 | 11 | 0.15 | Base |
| 3 | 1 | 17.4 | 11.9 | 68 | 1.1 | 0.0 | 0 | 0.24 | Base |
| 4 | 2 | 15.1 | 9.6 | 64 | 0.0 | 0.0 | 0 | 0.36 | Base |
| 5 | 8 | 2.0 | 0.4 | 20 | 0.0 | 0.0 | 0 | 0.38 | Base |
| 6 | 0.25 | 16.2 | 10.0 | 62 | 13.2 | 8.4 | 64 | 0.09 | 50% |
| 7 | 0.5 | 16.5 | 11.0 | 67 | 12.6 | 8.3 | 65 | 0.20 | 33% |
| 8 | 1 | 15.5 | 11.0 | 71 | 9.8 | 6.4 | 65 | 0.35 | 46% |
| 9 | 2 | 12.2 | 8.2 | 67 | 3.8 | 2.3 | 60 | 0.44 | 33% |
| 10 | 8 | 3.9 | 2.6 | 67 | 0.5 | 0.4 | 67 | 0.72 | 90% |

The results in Table 5 show that there was a clear advantage for operating with an inverse temperature profile which improved instantaneous selectivity at most space velocities for shorter operation times and consistently acted to prolong selectivity to benzene over longer operation times. This allowed for greater cumulative production in comparison to an isothermal bed at all space velocities While Examples 4 and 5 are directed to specific reactor types, similar improvement in selectivity would be exhibited for other reactor systems with an equivalent inverse temperature profile or temperature staging.

As demonstrated in the simulation, the yields, selectivities, and catalyst circulation rates were improved by the inventive concepts. In addition, the entire reaction may be accomplished in a single reaction zone thereby minimizing required equipment. Optionally, two or more reaction zones may be used.

As illustrated by Examples 4 and 5; the inverse temperature profile or temperature staging, enables the conversion of methane to higher hydrocarbons, e.g., aromatic compounds, at reduced aging/mechanical-attrition catalyst losses, improved operability, and higher selectivity; i.e., lower coke make; than the conventional fixed bed, and/or transport or riser configurations. In another embodiment, this invention relates to:

In another embodiment, this invention relates to

1. A process for converting methane to higher hydrocarbon(s) including aromatic hydrocarbon(s) in a reaction zone, the process comprising:
   (a) providing to said reaction zone a hydrocarbon feedstock containing methane;
   (b) providing a quantity of catalytic material within said reaction zone;
   (c) maintaining the said reaction zone with an inverse temperature profile; and
   (d) operating said reaction zone under reaction conditions sufficient to convert at least a portion of said methane to a first effluent having said higher hydrocarbon(s).

2. The process of paragraph 1, wherein said reaction zone is a moving bed reaction zone.

3. The process of paragraph 1, wherein said reaction zone is a fixed bed reaction zone.

4. The process of any of paragraphs 1-3, wherein said feedstock further comprises at least one of CO, $CO_2$, $H_2$, $H_2O$, and/or $O_2$.

5. The process of any of paragraphs 1-4, wherein a initial catalyzed reaction temperature is less than about 750° C.; preferably less than about 700° C.; alternately less than about 650° C.

6. The process of any of paragraphs 1-5, wherein a final catalyzed reaction temperature is greater than about 700° C.; preferably greater than about 800° C.; alternately greater than about 850° C.

7. The process of any of paragraphs 1-6, wherein sufficient quantity of catalytic material is provided so that the % approach to thermodynamic equilibrium conversion of methane to benzene at the reaction zone halfway point (in terms of quantity of catalytic material contacted by hydrocarbon) is greater than about 25%; preferably greater than about 50%; most preferably greater than about 75%.

8. The process of any of paragraphs 1-6, wherein sufficient quantity of catalytic material is provided so that the % approach to thermodynamic equilibrium conversion of methane to benzene at the reaction zone halfway point (in terms of half of the total differential temperature across the reaction zone) is greater than about 25%; preferably greater than about 50%; most preferably greater than about 75%.

9. The process of any of paragraphs 1-8, wherein said inverse temperature profile in said catalytic material is achieved by intermittent direct contact heating with combustion gases or an inert medium heated by said combustion gases.

10. The process of any of paragraphs 1-9, wherein said inverse temperature profile in said catalytic material is achieved by heat transfer through a heat transfer surface.

11. The process of paragraph 10, wherein heat transfer surface is heated by radiative and or conductive heat transfer from combustion.

12. The process of paragraph 10, wherein said heat transfer surface is a metal or ceramic.

13. The process of paragraph 10, wherein the catalytic material is located in one or more tubes in parallel and the tubes are located within a furnace providing heat to maintain said inverse temperature profile.
14. The process of paragraph 10, wherein the catalytic material is located in a vessel with one or more tubes passing through the bed; said tubes conveying combustion gas to maintain said inverse temperature profile.
15. The process of paragraph 2, wherein a portion of the catalytic material is withdrawn from the reaction zone; at least a portion of coke deposited on the catalytic material is removed by oxidation; and the catalytic material with a reduced level of coke is returned to the reaction zone.
16. The process of paragraph 2, wherein a portion of the catalytic material is withdrawn from the reaction zone; at least a portion of coke deposited on the catalytic material is removed by reaction with hydrogen to form methane; and the catalytic material with a reduced level of coke is returned to the reaction zone.
17. The process of paragraph 1, wherein cyclically the hydrocarbon feed is halted and an oxygen containing stream is instead supplied to the reaction zone so that at least a portion of coke deposited on the catalytic material is removed by oxidation; the oxygen containing stream is then halted; and the hydrocarbon feed is restarted.
18. The process of paragraph 1, wherein cyclically the hydrocarbon feed is halted and a hydrogen containing stream is instead supplied to the reaction zone so that at least a portion of coke deposited on the catalytic material is removed by conversion to methane; the hydrogen containing stream is then halted; and the hydrocarbon feed is restarted.
19. The process of any of paragraphs 1-18, wherein said catalytic material is a dehydrocyclization catalyst comprising a metal or compound thereof on an inorganic support.
20. The process of any of paragraphs 1-18, wherein said catalytic material comprises at least one of molybdenum, tungsten, rhenium, a molybdenum compound, a tungsten compound, a zinc compound, and a rhenium compound on ZSM-5, silica or an aluminum oxide.
21. A process for converting methane to higher hydrocarbon(s) including aromatic hydrocarbon(s) in two or more reaction zones operated in series, the process comprising:
  (a) providing a quantity of catalytic material within each reaction zone;
  (b) providing to a first reaction zone a hydrocarbon feedstock containing methane;
  (c) transfer at least a portion of the effluent of the said first reaction zone to a second reaction zone;
  (d) maintaining the first said reaction zone at a lower average temperature than said second reaction zone; and
  (e) operating said reaction zones under reaction conditions sufficient to convert at least a portion of said methane to a first effluent having said higher hydrocarbon(s).
22. The process of paragraph 21, wherein said reaction zones are moving bed reaction zones.
23. The process of paragraph 21, wherein said reaction zones are fixed bed reaction zones.
24. The process of any of paragraphs 21-23, wherein said feedstock further comprises at least one of CO, $CO_2$, $H_2$, $H_2O$, and/or $O_2$.
25. The process of any of paragraphs 21-24, wherein said initial catalyzed reaction temperature is less than about 750° C.; preferably less than about 700° C.; alternately less than about 650° C.
26. The process of any of paragraphs 21-25, wherein said final catalyzed reaction temperature is greater than about 700° C.; preferably greater than about 800° C.; alternately greater than about 850° C.
27. The process of any of paragraphs 21-26, wherein sufficient quantity of catalytic material is provide so that the % approach to thermodynamic equilibrium conversion of methane to benzene at the reaction zone halfway point (in terms of quantity of catalytic material contacted by hydrocarbon) is greater than about 25%; preferably greater than about 50%; most preferably greater than about 75%.
28. The process of paragraph 21-26, wherein sufficient quantity of catalytic material is provide so that the % approach to thermodynamic equilibrium conversion of methane to benzene at the reaction zone halfway point (in terms of half of the total differential temperature across the reaction zone) is greater than about 25%; preferably greater than about 50%; most preferably greater than about 75%.
29. The process of paragraph 21, wherein maintaining the first said reaction zone at a lower average temperature than said second reaction zone is achieved by heat transfer through a heat transfer surface in contact with the catalytic material in the reaction zones.
30. The process of paragraph 29, wherein the heat transfer surface is heated by radiative and or conductive heat transfer from combustion.
31. The process of paragraph 29, wherein said heat transfer surface is a metal or ceramic.
32. The process of paragraph 29, wherein the catalytic material is located in one or more tubes in parallel and the tubes are located within a furnace providing heat to maintain said inverse temperature profile.
33. The process of paragraph 29, wherein the catalytic material is located in a vessel with one or more tubes passing through the bed; said tubes conveying combustion gas to maintain said inverse temperature profile.
34. The process of paragraph 21, wherein maintaining the first said reaction zone at a lower average temperature than said second reaction zone is achieved by heating of the hydrocarbon stream by heat transfer through a heat transfer surface; said heating of the hydrocarbon stream be carried out between said reaction zones
35. The process of paragraph 22, wherein a portion of the catalytic material is withdrawn from the reaction zone; at least a portion of coke deposited on the catalytic material is removed by oxidation; and the catalytic material with a reduced level of coke is returned to the reaction zone.
36. The process of paragraph 22, wherein a portion of the catalytic material is withdrawn from the reaction zone; at least a portion of coke deposited on the catalytic material is removed by reaction with hydrogen to form methane; and the catalytic material with a reduced level of coke is returned to the reaction zone.
37. The process of paragraph 21, wherein cyclically the hydrocarbon feed is halted and an oxygen containing stream is instead supplied to the reaction zone so that at least a portion of coke deposited on the catalytic material is removed by oxidation; the oxygen containing stream is then halted; and the hydrocarbon feed is restarted.
38. The process of paragraph 21, wherein cyclically the hydrocarbon feed is halted and a hydrogen containing stream is instead supplied to the reaction zone so that at least a portion of coke deposited on the catalytic material is removed by conversion to methane; the hydrogen containing stream is then halted; and the hydrocarbon feed is restarted.

39. The process of paragraph 21-38, wherein said catalytic material is a dehydrocyclization catalyst comprising a metal or compound thereof on an inorganic support.

40. The process of claim 21-38, wherein said catalytic material comprises at least one of molybdenum, tungsten, rhenium, a molybdenum compound, a tungsten compound, a zinc compound, and a rhenium compound on ZSM-5, silica or an aluminum oxide.

41. The process of paragraph 16 or 36, wherein the reaction with hydrogen is conducted at a pressure greater than the pressure at which the methane containing feed is reacted to form aromatics.

42. The process of paragraph 16 or 36, wherein the reaction with hydrogen is conducted at a pressure of between about 150 kPa and about 5000 kPa.

43. The process of paragraph 1 or 21, wherein an aromatic product is recovered from the hydrocarbon product stream leaving a aromatic depleted, methane and $H_2$ residual stream.

44. The process of paragraph 43, wherein the said methane and $H_2$ residual stream is further processed such that at least a portion of the $H_2$ may be separated from the hydrocarbon stream by reaction with an oxygen containing species or utilizing physical separation technologies (such as cryogenic distillation, pressure swing adsorption, thermal swing adsorption, and or membrane systems); leaving a methane rich residual stream.

45. The process of paragraph 44, wherein at least a portion of said methane rich residual stream is recycled to said reaction zone.

46. The process of paragraph 43, wherein the said recovered aromatic products are further processed by reaction with an alkylation agent to produce alkylated aromatics.

47. The process of paragraph 43, wherein the said recovered aromatic products are further processed by reaction with a $H_2$ containing stream to produce hydrogenated species or alky aromatics.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

Certain embodiments and features have been described using a set of numerical upper limits and a set of numerical lower limits. It should be appreciated that ranges from any lower limit to any upper limit are contemplated unless otherwise indicated. Certain lower limits, upper limits and ranges appear in one or more claims below. All numerical values are "about" or "approximately" the indicated value, and take into account experimental error and variations that would be expected by a person having ordinary skill in the art.

Various terms have been defined above. To the extent a term used in a claim is not defined above, it should be given the broadest definition persons in the pertinent art have given that term as reflected in at least one printed publication or issued patent. Furthermore, all patents, test procedures, and other documents, including priority documents, cited in this application are fully incorporated by reference to the extent such disclosure is not inconsistent with this application and for all jurisdictions in which such incorporation is permitted.

While the foregoing is directed to embodiments of the present invention, other and further embodiments of the invention may be devised without departing from the basic scope thereof, and the scope thereof is determined by the claims that follow.

What is claimed is:

1. A process for converting methane to higher hydrocarbon(s) including aromatic hydrocarbon(s) in a reaction zone, the process comprising:
   (a) providing to said reaction zone a hydrocarbon feedstock containing methane;
   (b) providing a quantity of catalytic material within said reaction zone;
   (c) maintaining the said reaction zone with an inverse temperature profile; and
   (d) operating said reaction zone under reaction conditions sufficient to convert at least a portion of said methane to a first effluent having said higher hydrocarbon(s) wherein sufficient quantity of catalytic material is provided so that the percentage approach thermodynamic equilibrium conversion of methane to benzene at the reaction zone halfway point (in terms of quantity of catalytic material contracted by hydrocarbon) is greater than about 25%.

2. The process of claim 1, wherein said reaction zone is a moving bed reaction zone.

3. The process of claim 1, wherein said reaction zone is a fixed bed reaction zone.

4. The process of claim 1, wherein said feedstock further comprises at least one of CO, $CO_2$, $H_2$, $H_2O$, and/or $O_2$.

5. The process of claim 1, wherein a initial catalyzed reaction temperature is less than about 750° C.

6. The process of claim 1, wherein a final catalyzed reaction temperature is greater than about 700° C.

7. The process of claim 1, wherein sufficient quantity of catalytic material is provide so that the % approach to thermodynamic equilibrium conversion of methane to benzene at the reaction zone halfway point (in terms of half of the total differential temperature across the reaction zone) is greater than about 25%.

8. The process of claim 1, wherein said inverse temperature profile is achieved by intermittent direct contact heating with combustion gases or an inert medium heated by said combustion gases.

9. The process of claim 1, wherein said inverse temperature profile is achieved by heat transfer through a heat transfer surface.

10. The process of claim 9, wherein heat transfer surface is heated by radiative and or conductive heat transfer from combustion.

11. The process of claim 9, wherein said heat transfer surface is a metal or ceramic.

12. The process of claim 9, wherein the catalytic material is located in one or more tubes in parallel and the tubes are located within a furnace providing heat to maintain said inverse temperature profile.

13. The process of claim 9, wherein the catalytic material is located in a vessel with one or more tubes passing through the bed; said tubes conveying combustion gas to maintain said inverse temperature profile.

14. The process of claim 2, wherein a portion of the catalytic material is withdrawn from the reaction zone; at least a portion of coke deposited on the catalytic material is removed by oxidation; and the catalytic material with a reduced level of coke is returned to the reaction zone.

15. The process of claim 2, wherein a portion of the catalytic material is withdrawn from the reaction zone; at least a portion of coke deposited on the catalytic material is removed by reaction with hydrogen to form methane; and the catalytic material with a reduced level of coke is returned to the reaction zone.

16. The process of claim 3, wherein cyclically the hydrocarbon feed is halted and an oxygen containing stream is instead supplied to the reaction zone so that at least a portion of coke deposited on the catalytic material is removed by oxidation; the oxygen containing stream is then halted; and the hydrocarbon feed is restarted.

17. The process of claim 3, wherein cyclically the hydrocarbon feed is halted and a hydrogen containing stream is instead supplied to the reaction zone so that at least a portion of coke deposited on the catalytic material is removed by conversion to methane; the hydrogen containing stream is then halted; and the hydrocarbon feed is restarted.

18. The process of claim 1, wherein said catalytic material is a dehydrocyclization catalyst comprising a metal or compound thereof on an inorganic support.

19. The process of claim 1, wherein said catalytic material comprises at least one of molybdenum, tungsten, rhenium, a molybdenum compound, a tungsten compound, a zinc compound, and a rhenium compound on ZSM-5, silica or an aluminum oxide.

20. The process of claim 1, wherein said initial catalyzed reaction temperature is less than about 650° C.

21. The process of claim 1, wherein said final catalyzed reaction temperature is greater than about 850° C.

22. The process of claim 1, wherein sufficient quantity of catalytic material is provide so that the % approach to thermodynamic equilibrium conversion of methane to benzene at the reaction zone halfway point (in terms of quantity of catalytic material contacted by hydrocarbon) is greater than about 75%.

23. The process of claim 1, wherein sufficient quantity of catalytic material is provide so that the % approach to thermodynamic equilibrium conversion of methane to benzene at the reaction zone halfway point (in terms of half of the total differential temperature across the reaction zone) is greater than about 75%.

* * * * *